United States Patent
Simons et al.

(10) Patent No.: US 11,031,138 B2
(45) Date of Patent: Jun. 8, 2021

(54) SYSTEM AND METHOD FOR GENERATING DATA RESOURCES IN A PROCESSING SYSTEM

(71) Applicant: Surescripts LLC, Arlington, VA (US)

(72) Inventors: Bradley Carter Simons, Rosemount, MN (US); David Williams, Beaverton, OR (US); Keith Edward Willard, Saint Paul, MN (US)

(73) Assignee: SURESCRIPTS LLC, Arlington, VA (US)

( * ) Notice: Subject to any disclaimer, the term of this patent is extended or adjusted under 35 U.S.C. 154(b) by 587 days.

(21) Appl. No.: 15/481,209

(22) Filed: Apr. 6, 2017

(65) Prior Publication Data

US 2018/0293351 A1 Oct. 11, 2018

(51) Int. Cl.
*G16H 70/00* (2018.01)
*G16H 15/00* (2018.01)

(52) U.S. Cl.
CPC ............ *G16H 70/00* (2018.01); *G16H 15/00* (2018.01)

(58) Field of Classification Search
CPC ............................... G16H 70/00; G16H 15/00
See application file for complete search history.

(56) References Cited

U.S. PATENT DOCUMENTS

| | | | |
|---|---|---|---|
| 10,331,667 B2 * | 6/2019 | Jarman | G06F 16/3331 |
| 2004/0054690 A1 * | 3/2004 | Hillerbrand | G06Q 10/06 |
| 2014/0013205 A1 * | 1/2014 | Mikhaiel | G06F 17/2247 |
| | | | 715/234 |
| 2015/0066536 A1 * | 3/2015 | Spates | G06F 17/2705 |
| | | | 705/3 |
| 2016/0283667 A1 * | 9/2016 | Rachapalli | H04L 63/10 |
| 2017/0103163 A1 * | 4/2017 | Emanuel | G06F 16/23 |

* cited by examiner

*Primary Examiner* — Aleksandr Kerzhner
*Assistant Examiner* — Maher N Algibhah
(74) *Attorney, Agent, or Firm* — Fiala & Weaver, P.L.L.C.

(57) ABSTRACT

Systems and methods, as well as devices, are described for clinical resource generation. CCDA documents that include clinical information and observations are utilized to generate FHIR model instances that are specific to the CCDA documents. Path definitions are assigned for each information-value pair the CCDA documents that define mappings between the information-value pairs and objects of FHIR model instances. Objects for the instance models are created, and values are provided to the objects representative of the information-value pairs. Groups of objects are provided in FHIR resource bundles that are stored in a database which may be queried against to provide specific FHIR resources upon request. Requests for clinical information may be used to trigger the generation of the FHIR resource bundles.

18 Claims, 6 Drawing Sheets

US 11,031,138 B2

SYSTEM AND METHOD FOR GENERATING DATA RESOURCES IN A PROCESSING SYSTEM

BACKGROUND

I. Technical Field

The present subject matter relates to clinical resource generation.

II. Background Art

Clinical Document Architecture (CDA) is an HL7 ("Health Level Seven International") standard for building electronic clinical documents. Consolidated-CDA (C-CDA or CCDA) was subsequently developed to address shortcomings with the original CDA standard. CCDA document formats are a common way to exchange clinical information, in part due to the Meaningful Use Stage Two (MU2) criteria which call out use of C-CDA documents for particular types of information exchange.

Fast Healthcare Interoperability Resources (FHIR) is a recent standard for clinical messaging/interoperability in which healthcare information is conveyed electronically (see https://www.hl7.org/fhir/overview.html). FHIR provides, at its base level, a certain degree of specificity for fundamental atoms of information in clinical messaging, thus providing a representation for clinical information that allows for interchange of information at levels more granular than an entire document. The basic FHIR standard allows for specific profiles of information to be used by different entities.

BRIEF SUMMARY

Methods, systems, and apparatuses are described for clinical resource generation using ontology models in processing systems, substantially as shown in and/or described herein in connection with at least one of the figures, as set forth more completely in the claims.

BRIEF DESCRIPTION OF THE DRAWINGS/FIGURES

The accompanying drawings, which are incorporated herein and form a part of the specification, illustrate embodiments and, together with the description, further serve to explain the principles of the embodiments and to enable a person skilled in the pertinent art to make and use the embodiments.

Embodiments will now be described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION

I. Introduction

Figure 1:
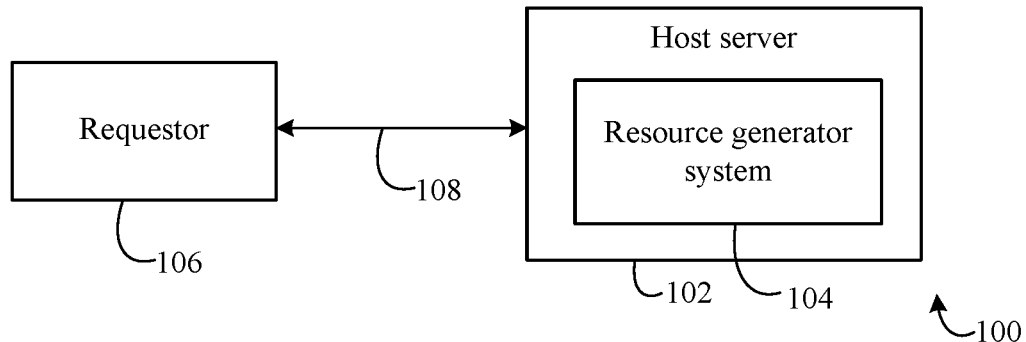
FIG. 1 shows a block diagram of a computer system that includes a resource generator system, according to an example embodiment.

The present specification discloses numerous example embodiments. The scope of the present patent application is not limited to the disclosed embodiments, but also encompasses combinations of the disclosed embodiments, as well as modifications to the disclosed embodiments.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Furthermore, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner.

Still further, it should be noted that the drawings/figures are not drawn to scale unless otherwise noted herein.

Numerous exemplary embodiments are now described. Any section/subsection headings provided herein are not intended to be limiting. Embodiments are described throughout this document, and any type of embodiment may be included under any section/subsection. Furthermore, it is contemplated that the disclosed embodiments may be combined with each other in any manner. That is, the embodiments described herein are not mutually exclusive of each other and may be practiced and/or implemented alone, or in any combination.

II. Example Embodiments

The example techniques and embodiments described herein may be adapted to various types of systems and devices, for example but without limitation, computing systems (e.g., computers/computing devices such as desktops, laptops, etc., and servers, enterprise computing systems, etc.), communication devices (e.g., cellular and smart phones, etc.), and/or the like, that communicate information, such as in accordance with communication standards. For instance, computing systems that communicate over a network and exchange clinical information in accordance with the CCDA standard may be configured according to the described embodiments and techniques. While the embodiments herein may be described with respect to various computing systems and implementations as conceptual and/or illustrative examples for descriptive consistency, other types of electronic and communication devices and implementations are also contemplated for implementing the disclosed techniques. It is contemplated herein that in various embodiments and with respect to the illustrated figures of this disclosure, one or more components described and/or shown may not be included and that additional components may be included.

The example techniques and embodiments described herein provide for clinical resource generation using ontology models, e.g., such as FHIR resource generation using ontology models that map to information contained in CCDA documents, in processing systems. The processing systems may be a host entity such as a server or host server, as well as other server/client processing devices of requestors for clinical resource generation, e.g., computing devices, of a trading partner(s), a vendor service(s), a doctor or doctor's office (including nurses and/or other staff), and/or another third-party entity(ies). The processing systems and/or users thereof may receive CCDA documents (e.g., in extensible markup language (XML) format) containing clinical information about various patients. The clinical information may include information like patient name, address, title, contact information, age, gender, clinical observations from doctor visits (e.g., weight, temperature, blood pressure, symptoms, diagnoses, and/or the like), prescriptions of the patient, etc. CCDA provides a structured identification system for clinical information using identifiers, e.g., tags, paired with information strings. For instance, an example patient name may be represented in a CCDA document as:

```
<patient>
  <name>
    <given>Paulina</given>
    <family>Coffin</family>
  </name>
  ...
</patient>
```

Such identifiers and associated strings may be referred to herein as information-value pairs where the identifier tag describes of what type the information is and the value is the string. It should be noted that for a given type of information in an information-value pair, many values may be included in a CCDA for different people associated with the clinical data, such as, but without limitation, doctors, nurses, patients, legal guardians, etc.

However, the organizational structure of information in CCDA documents is not strictly defined. As an example, a patient name, such as the patient name noted above, may be included at different sections for different CCDA documents of various patients. As another example, an observation in one section of a CCDA document may be contained within organizer/composition components, but in another section be contained in act/entryRelationship components, and in yet other sections the observation information may be in neither these components. Hence, the program needs to be able to handle all the structures in a CCDA within which an observation may occur. In other words, names, dates, observations, and other information of interest to insurance providers, doctors/prescribers, pharmacists, pharmacy benefits management (PBM) entities, and/or other types of health care providers, may reside in various parts of any given CCDA document. Compounding this issue is the sheer volume of data that may be included in a given CCDA document, which essential, which may include tens or even hundreds of pages of clinical information without predictable organization.

For instance, continuing with the patient name example above, a CCDA document ("Example CCDA Document") for a single clinical observation, a measured body weight, for the patient is provided as follows:

```
<?xml-stylesheet type="text/xsl" href="https://name.caregroup.org/dyna/CCDA/CDA.XSL"?>
<ClinicalDocument xmlns="urn:h17-org:v3" xmlns:cda="urn:h17-org:v3" xmlns:gsd="http://aurora.regenstrief.org/GenericXMLSchema" xmlns:sch="http://www.ascc.net/xml/schematron" xmlns:xlink="http://www.w3.org/TR/WD-xlink" xmlns:sdtc="urn:h17-org:sdtc" xmlns:mif="urn:h17-org:v3/mif" xmlns:xsi="http://www.w3.org/2001/XMLSchema-instance" xsi:schemaLocation="urn:h17-org:v3 CDA_Schema_Files\infrastructure\cda\CDA_SDTC.xsd">
  <realmCode code="US" />
  <typeId root="2.16.840.1.113883.1.3" extension="POCD_HD000040" />
  <templateId root="2.16.840.1.113883.10.20.22.1.1" />
  <templateId root="2.16.840.1.113883.10.20.22.1.2" />
  <id root="2.16.840.1.113883.3.186.1" extension="102481-20140908161003001" />
  <code code="34111-5" codeSystem="2.16.840.1.113883.6.1" displayName="Evaluation and Management Note" />
  <title>Boston General Hospital Emergency Department Visit Summary Document</title>
  <effectiveTime value="20140908161003-0400" />
  <confidentialityCode code="N" codeSystem="2.16.840.1.113883.5.25" />
  <languageCode code="en-US" />
  <recordTarget>
    <patientRole>
      <id extension="56566965" root="2.16.840.1.113883.3.186.2" />
      <addr>
        <streetAddressLine>384 CHESTNUT PLACE APT 617</streetAddressLine>
        <city>MELROSE</city>
        <state>MA</state>
        <postalCode>02176</postalCode>
      </addr>
      <telecom use="HP" value="341-605-7453" />
      <patient>
        <name>
          <given>Paulina </given>
          <family>Coffin</family>
        </name>
        <administrativeGenderCode code="M" codeSystem="2.16.840.1.113883.5.1" />
        <birthTime value="19840313" />
        <raceCode code="2054-5" displayName="Black or African American" codeSystem="2.16.840.1.113883.6.238" />
        <ethnicGroupCode code="2186-5" displayName="Not Hispanic or Latino" codeSystem="2.16.840.1.113883.6.238" />
        <languageCommunication>
          <languageCode code="eng" />
          <preferenceInd value="true" />
        </languageCommunication>
      </patient>
      <providerOrganization>
        <id root="2.16.840.1.113883.3.186" />
        <name>Boston General Hospital</name>
        <telecom />
        <addr></addr>
      </providerOrganization>
    </patientRole>
  </recordTarget>
<author>
  <time value="20140908161003-0400" />
  <assignedAuthor>
    <id root="2.16.840.1.113883.4.6" extension="3427662367" />
    <addr></addr>
    <telecom />
    <assignedPerson>
      <name>
```

```xml
        <prefix>Dr. </prefix>
        <given>Paulina </given>
        <family>Mendoza</family>
        <suffix qualifier="TITLE">MD</suffix>
      </name>
    </assignedPerson>
    <representedOrganization>
      <id root="2.16.840.1.113883.3.96.1.3" extension="2.16.840.1.113883.3.186" />
      <name>Boston General Hospital</name>
      <telecom />
      <addr></addr>
    </representedOrganization>
  </assignedAuthor>
</author>
<custodian>
  <assignedCustodian>
    <representedCustodianOrganization>
      <id root="2.16.840.1.113883.3.186" />
      <name>Boston General Hospital</name>
      <telecom />
      <addr></addr>
    </representedCustodianOrganization>
  </assignedCustodian>
</custodian>
<informationRecipient>
  <intendedRecipient>
    <addr />
    <informationRecipient>
      <name />
    </informationRecipient>
    <receivedOrganization>
      <id root="2.16.840.1.113883.3.96.1.3" extension="" />
      <name />
      <telecom />
      <addr />
    </receivedOrganization>
  </intendedRecipient>
</informationRecipient>
<legalAuthenticator>
  <time value="20140908161003-0400" />
  <signatureCode code="S" />
  <assignedEntity>
    <id root="2.16.840.1.113883.4.6" extension="7132864366" />
    <addr></addr>
    <telecom />
    <assignedPerson>
      <name>
        <prefix>Dr. </prefix>
        <given>Amanda </given>
        <family>Mendoza</family>
        <suffix qualifier="TITLE">MD</suffix>
      </name>
    </assignedPerson>
    <representedOrganization>
      <id root="2.16.840.1.113883.3.186" />
      <name>Boston General Hospital</name>
      <telecom />
      <addr></addr>
    </representedOrganization>
  </assignedEntity>
</legalAuthenticator>
<participant></participant>
<documentationOf>
  <serviceEvent classCode="PCPR">
    <effectiveTime>
      <low value="201407021900-0400" />
      <high value="201407030019-0400" />
    </effectiveTime>
    <performer typeCode="PRF">
      <functionCode code="PR" codeSystem="2.16.840.1.113883.12.443" />
      <assignedEntity>
        <id root="2.16.840.1.113883.4.6" extension="7132864366" />
        <id root="2.16.840.1.113883.3.72.5.2" extension="7132864366" />
        <addr />
        <telecom />
        <assignedPerson>
          <name>
            <given>Amanda </given>
            <family>Mendoza</family>
            <suffix qualifier="TITLE">NP</suffix>
          </name>
        </assignedPerson>
      </assignedEntity>
    </performer>
    <performer typeCode="PRF">
      <functionCode code="PR" codeSystem="2.16.840.1.113883.12.443" />
      <assignedEntity>
        <id root="2.16.840.1.113883.4.6" extension="7132864366" />
        <id root="2.16.840.1.113883.3.72.5.2" extension="7132864366" />
        <addr />
        <telecom />
        <assignedPerson>
          <name>
            <prefix>Dr. </prefix>
            <given>Amanda </given>
            <family>Hachem</family>
            <suffix qualifier="TITLE">MD</suffix>
          </name>
        </assignedPerson>
      </assignedEntity>
    </performer>
    <performer typeCode="PRF">
      <functionCode code="PR" codeSystem="2.16.840.1.113883.12.443" />
      <assignedEntity>
        <id root="2.16.840.1.113883.4.6" extension="1855165365" />
        <id root="2.16.840.1.113883.3.72.5.2" extension="1855165365" />
        <addr />
        <telecom />
        <assignedPerson>
          <name>
            <given>Maisa </given>
            <family>Hachem</family>
            <suffix qualifier="TITLE">NP</suffix>
          </name>
        </assignedPerson>
      </assignedEntity>
    </performer>
    <performer typeCode="PRF">
      <functionCode code="PR" codeSystem="2.16.840.1.113883.12.443" />
      <assignedEntity>
        <id root="2.16.840.1.113883.4.6" extension="1855165365" />
        <id root="2.16.840.1.113883.3.72.5.2" extension="1855165365" />
        <addr />
        <telecom />
        <assignedPerson>
          <name>
            <prefix>Dr. </prefix>
            <given>Maisa </given>
            <family>Washington</family>
            <suffix qualifier="TITLE">MD</suffix>
          </name>
        </assignedPerson>
      </assignedEntity>
    </performer>
  </serviceEvent>
</documentationOf>
<componentOf>
  <encompassingEncounter>
    <id extension="42884028 4" root="2.16.840.1.113883.3.186.9" />
    <effectiveTime>
      <low value="20140702" />
      <high value="20140704" />
    </effectiveTime>
    <dischargeDispositionCode code="09"
```

-continued

```
codeSystem="2.16.840.1.113883.6.21" displayName="Routine
Discharge" codeSystemName="UB92">
            <originalText>ADMITTED</originalText>
        </dischargeDispositionCode>
    </encompassingEncounter>
</componentOf>
<component>
    <structuredBody>
        <component>
            <section>
                <templateId root="2.16.840.1.113883.10.20.22.2.4.1" />
                <code code="8716-3" codeSystem="2.16.840.1.113883.6.1"
/>
                <title>Vital Signs</title>
                <text></text>
                <entry typeCode="COMP">
                    <organizer classCode="CLUSTER" moodCode="EVN">
                        <templateId root="2.16.840.1.113883.10.20.22.4.26"
/>
                        <id root="2.16.840.1.113883.3.186.3"
extension="102481-S-3-dt-14003" />
                        <code code="46680005"
codeSystem="2.16.840.1.113883.6.96" displayName="Vital signs"
codeSystemName="SNOMED CT" />
                        <statusCode code="completed" />
                        <effectiveTime value="20140703" />
                        <component>
                            <observation classCode="OBS" moodCode="EVN">
                                <templateId
root="2.16.840.1.113883.10.20.22.4.27" />
                                <id root="2.16.840.1.113883.3.186.3"
extension="102481-OMR-19" />
                                <code code="3141-9"
codeSystem="2.16.840.1.113883.6.1" codeSystemName="LOINC"
displayName="BODY WEIGHT (MEASURED)" />
                                <text>
                                    <reference value="#vit-1" />
                                </text>
                                <statusCode code="completed" />
                                <effectiveTime value="20140703" />
                                <value xsi:type="PQ" value="144.84"
unit="[lb_av]" />
                            </observation>
                        </component>
                    </organizer>
                </entry>
            </section>
        </component>
    </structuredBody>
</component>
</ClinicalDocument>
```

The FHIR standard was promulgated to provide for communications having a certain degree of specificity for fundamental atoms of information in clinical messaging. That is, messaging between computer systems and querying databases that use FHIR includes the exchange and querying of clinical information that may relate to a number of defined "resources" associated with patients, practitioners, appointments, clinical observations, clinical documents, medications, accounts, and/or the like, as defined by the FHIR standard. For instance, FHIR patient resources may include information about a patient like patient name, address, title, contact information, age, gender, clinical observations from doctor visits (e.g., measured body weight, temperature, and blood pressure, symptoms, diagnoses, and/or the like), prescriptions of the patient, etc. A FHIR resource also utilizes libraries with objects that represent the resource. Generally, FHIR resources also include metadata (e.g., in formats such as, but without limitation, XML format) that describes different aspects of the resources. That is, the metadata may describe the structure and components of the resource (e.g., properties of the resource such as, but not limited to, a first property for a resource being an identification field, while a second property for the resource is a patient's last name, and a third property for the resource is a patient's first name, etc.), rather than actual informational values associated the resource (e.g., Resource ID=123456, Last name="Berger", and First name="Devin").

As described herein with respect to embodiments, clinical information may be exchanged between computer systems and/or queried against a database of FHIR resources according to the FHIR standard. Utilizing a standard Resource Description Framework (RDF) model, along with mapping information corresponding to a CCDA document, instances of FHIR resources and resource bundles for specific information from CCDA documents, including but not limited to clinical observations, can be automatically generated according to the described techniques and embodiments herein.

For instance, in FIG. 1, a block diagram of a network of computer systems 100 that includes a resource generator system 104 is shown, according to an embodiment. Network of computer systems 100 includes a host server 102 that may include one or more processing devices such as, but not limited to, servers, resource generator system 104, and a requestor system 106 that may also include one or more processing devices such as, but not limited to, servers and client devices such as laptop/desktop computers and computer terminals, personal handheld devices, etc. Host server 102 may be communicatively coupled or linked to requestor system 106 via a communication link 108.

Host server 102 may comprise one or more computers/servers of a host entity facilitating access to resource generator system 104 by remote computer systems such as requestor system 106, according to embodiments. Host server 102 may include geographically distributed computers/servers, a rack server system(s), a stand-alone server, etc.

Requestor system 106 may comprise one or more computers/servers of an entity, such as a trading partner(s), a vendor service(s), a doctor or doctor's office (including nurses and/or other staff), as noted above, that desires to request clinical resource generation related to CCDA documents for patients from host server 102 over communication link 108.

Communication link 108 may comprise at least one network or direct communication connection, or any combination thereof, between host server 102 and requestor system 106 that enables communication messages such as requests for generation of clinical resources and associated responses, as described herein, to be exchanged. As used herein, the term "messages" includes resources such as clinical resources, data, information, packets, and/or the like, related to messaging such as clinical messaging, transmitted and/or received according to any communication standard or protocol, or according to ad hoc communications. In embodiments, communication link 108 may comprise wired and/or wireless portions of one or more networks such as networks of the host entity and requestors, including enterprise networks, the Internet, etc.

Resource generator system 104 may comprise hardware and/or software components configured to automatically generate clinical resources, as described herein. For instance, in embodiments, resource generator system 104 is configured to automatically generate clinical resources, e.g., based on the FHIR standard (FHIR resources), at host server 102 based on a request from remote computer system 106, although it is contemplated herein that resource generator system 104 is also configured to generate resources without explicit requests therefor. Resource generator system 104 is configured to perform this function by utilizing an ontology model (e.g., through RDF) of the FHIR standard with information in one or more documents, e.g., CCDA documents, received from remote computer system 106, and/or stored at host server 102. The ontology model is a uniform RDF model for the FHIR standard, as described herein, and provides a characterization of relationships within the FHIR standard, FHIR resources, and FHIR resource values. After a CCDA document is utilized to automatically generate an object model document having information-value pairs for data thereof by resource generator system 104, resource generator system 104 automatically assigns path definitions for the information-value pairs to map the pairs to objects in the ontology model. Resource generator system 104 is configured to then automatically generate an instance model for the FHIR standard that is specific to the CCDA document based on the mapping. The instance model includes corresponding clinical resources according to the FHIR standard for each of the information-value pairs.

Generated instance models may be stored by resource generator system 104 in one or more processing devices and/or storage devices described herein. When stored, the instance models may be utilized when queries from requestors or processing devices of the host entity are received for specific clinical resources associated with patients, e.g., upon being saved in one or more databases. Additionally, the instance models may be utilized to generate FHIR resources and/or FHIR resource bundles, as described in further detail below.

Resource generator system 104 is also configured to automatically cause activation of a communication interface (not shown but described elsewhere herein) to execute functionality thereof and provide FHIR resources and/or FHIR resource bundles to requestors, e.g., over communication link 108.

It is contemplated herein, according to embodiments, that host server 102 and resource generator system 104 may together comprise one or more servers that perform the described functionality of resource generator system 104, as well as other functionality for a host entity, or may be a single server performing either or both of these types of functionality. Other relational configurations of host server 102 and resource generator system 104 are also contemplated herein, as would be understood by a person of skill in the relevant art(s) having the benefit of this disclosure.

Figure 2:
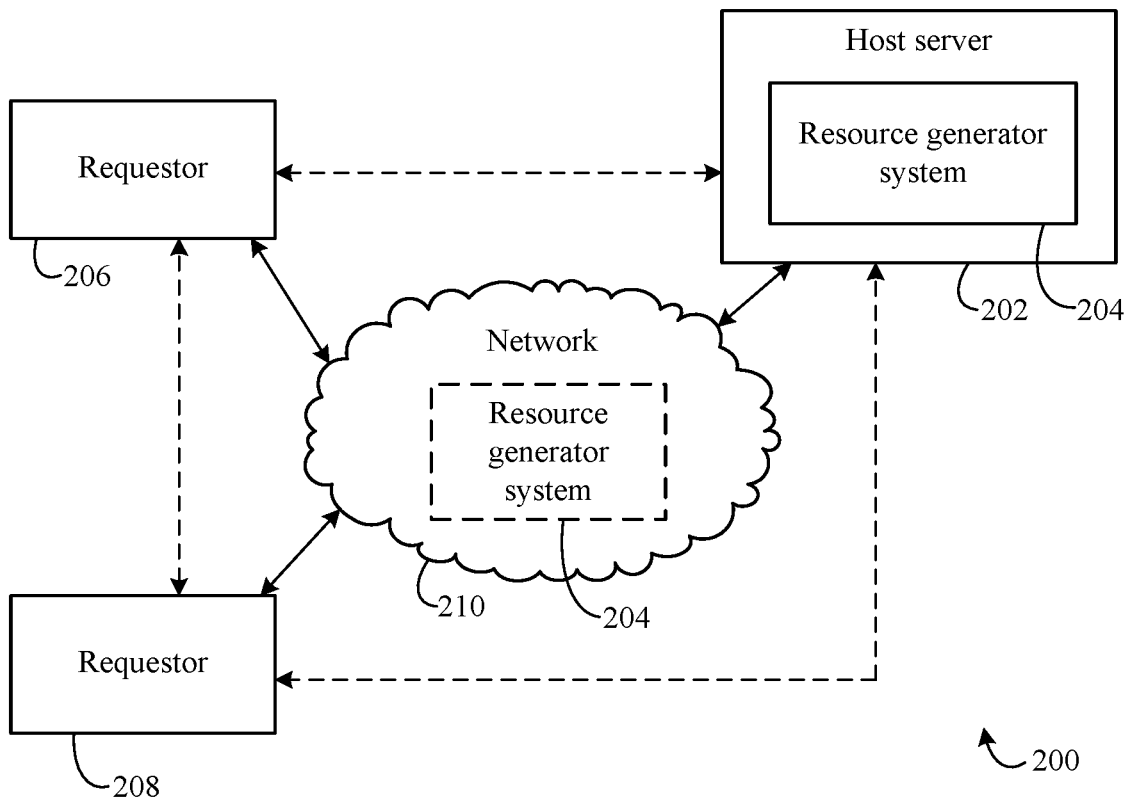
FIG. 2 shows a block diagram of a network of computer systems that includes a resource generator system, according to an example embodiment.

Turning now to FIG. 2, a block diagram of a network of computer systems 200 that includes a resource generator system 204 is shown, according to an embodiment. Network of computer systems 200 may be a further embodiment of network of computer systems 100 of FIG. 1. Network of computer systems 200 includes a host server 202, resource generator system 204, a requestor 206, and a requestor 208. Host provider 202, requestor 206, and requestor 208 may be communicatively coupled or linked each other via a network 210.

Host server 202 may be a further embodiment of host server 102 of FIG. 1, and, for the purposes of illustration for FIG. 2, is configured the same, or substantially the same, as host server 102 above. Resource generator system 204 may be a further embodiment of resource generator system 104 of FIG. 1, and, for the purposes of illustration for FIG. 2, is configured the same, or substantially the same, as resource generator system 104 above. Requestor 206 and requestor 208 may each be a further embodiment of requestor 106 of FIG. 1, and for the purposes of illustration for FIG. 2 is configured the same, or substantially the same, as requestor 106 above.

Network 210 may be a further embodiment of communication link 108 of FIG. 1. Network 210 may comprise at least one network and/or direct connection (i.e., a communication link), or any combination thereof. That is, network 210 may be any combination of the Internet, the "cloud," direct communication links, business and/or enterprise networks, and/or the like.

As noted, network 210 is configured to communicatively couple host server 202, requestor 206, and requestor 208 to each other. Accordingly, network of computer systems 200 is configured as a further embodiment of network of computer systems 100 in that resource generator system 204 is configured to automatically generate FHIR resources and FHIR resource bundles based on CCDA documents received from any system communicatively coupled to resource generator system 204, including host server 202, requestor 206, and requestor 208, similarly as described above for resource generator system 104 of FIG. 1.

For instance, an example scenario is now described in the context of network of computer devices 200 as shown in FIG. 2. Host server 202 may receive one or more CCDA documents and/or requests/queries for clinical information from requestor 206 and/or requestor 208. Requestor 206 and/or requestor 208 may provide one or more CCDA documents from which resource generator system 204 generates FHIR resources and/or FHIR resource documents, or requestor 206 and/or requestor 208 may request/query resource generator system 204 for clinical information in FHIR format that was previously provided to resource generator system 204 in one or more CCDA documents. For example, a health care provider may provide the Example CCDA Document shown above on for patient Paulina Coffin that includes a measured body weight clinical observation. Subsequently, requestor 206 may provide a request/query to host server 202 for a FHIR resource corresponding to the last measured body weight observation for the patient. Prior to, or responsive to, the request/query from requestor 206, resource generator system 204 may utilize the Example CCDA Document to generate a FHIR instance model corresponding thereto, and to generate a consumable FHIR resource or FHIR resource bundle to be returned to requestor 206.

Further extending this example, subsequent to the FHIR resource or FHIR resource bundle being returned to requestor 206, requestor 208 may also request/query host server 202 for the measured body weight clinical observation of the patient. Resource generator system 204 may provide the already-generated FHIR resource or FHIR resource bundle to requestor 208.

Still referring to FIG. 2, while shown for illustrative simplicity and brevity as including a single host provider (e.g., host server 202) and two remote computer systems (requestors 206/208), it is contemplated herein that network of computer systems 200 may include more or fewer of any of these components in embodiments.

The described techniques and embodiments provide for automatically generating clinical observation resources, e.g., in a FHIR format, from documents that are not in the FHIR format, e.g., CCDA documents. The described embodiments and techniques allow for reduced development time from IT/engineering teams of an entity for creating FHIR models of CCDA documents from which FHIR resources and FHIR resource bundles are generated. The described embodiments and techniques may be configured and scaled to accommodate multiple CCDA documents, as well as different document formatting standards, such as, but not limited to, CCDA and FHIR.

Systems, devices, and apparatuses contemplated herein, such as systems, devices, and apparatuses that include resource generator systems and/or components thereof, may be configured in various ways for generating clinical resource information objects according to the described techniques and embodiments, e.g., from CCDA documents. Techniques and embodiments are provided for implementation in and with devices, apparatuses, and systems that utilize networks to communicate with other devices, apparatuses, and systems. For instance, in embodiments, resource generator systems according to the described techniques and embodiments may be implemented in devices, apparatuses, and systems such as those enumerated herein, to generate clinical resource information objects for unrelated computer systems over a communication link such as a network or the Internet.

The techniques and embodiments described herein provide for improvements in generating clinical resource information objects, such as but without limitation, generating clinical resource information objects according to the FHIR standard from CCDA documents.

For instance, methods, systems, circuits, devices, and apparatuses are provided for resource generator systems. A system in accordance with an example aspect is described. The system includes a memory configured to store program instructions, and at least one processor configured to execute the program instructions to perform a method. The method performed includes receiving a document that includes clinical information and that is structured in accordance with a first standard format, and generating an object model document to include at least one information-value pair of a plurality information-value pairs that each comprise an information identifier and an associated value string that are included in the document. The method also includes assigning path definitions for each of the at least one information-value pair that define mappings between the at least one information-value pair in the object model document and objects of an ontology model having a second standard format, and generating an instance model of the ontology model that is representative of the document and that is in the second standard format based on the path definitions. The generating further includes creating objects for the instance model, and providing values to the objects for the instance model corresponding to each of the at least one information-value pair.

In embodiments, the method of the system further includes generating resources in accordance with the second standard format from the objects for the instance model.

In embodiments, in the method of the system, creating objects for the instance model includes creating a number of objects based on a request for information that corresponds to a same number of information-value pairs.

In embodiments, in the method of the system, the first standard format is CCDA (Consolidated Clinical Document Architecture) and the second standard format FHIR (Fast Healthcare Interoperability Resources).

In embodiments, the method of the system further includes generating a FHIR resource bundle, that includes the clinical information represented in the document, as FHIR resources within a FHIR document resource. In embodiments, the method of the system further includes storing the FHIR resource bundle in a database, and providing access to the database to accept queries for specific ones of the FHIR resources. In embodiments, in the method of the system, the document is one of a plurality of documents in accordance with the first standard format that are stored in a repository, and a first information identifier of a first information-value pair in a first section of the document is the same as a second information identifier of a second information-value pair in a second section of another document in the repository.

In embodiments, in the method of the system, the ontology model comprises an RDF model.

A computer-implemented method in accordance with an example aspect is described. The method includes receiving a document that includes clinical information and that is structured in accordance with a first standard format, and generating an object model document to include at least one information-value pair of a plurality information-value pairs that each comprise an information identifier and an associated value string that are included in the document. The method also includes assigning path definitions for each of the at least one information-value pair that define mappings between the at least one information-value pair in the object model document and objects of an ontology model having a second standard format, and generating an instance model of the ontology model that is representative of the document and that is in the second standard format based on the path definitions. The generating further includes creating objects for the instance model, and providing values to the objects for the instance model corresponding to each of the at least one information-value pair.

In embodiments, the computer-implemented method further includes generating resources in accordance with the second standard format from the objects for the instance model.

In embodiments, in the computer-implemented method, creating objects for the instance model includes creating a number of objects based on a request for information that corresponds to a same number of information-value pairs.

In embodiments, in the computer-implemented method, the first standard format is CCDA and the second standard format is FHIR, and the method further includes generating a FHIR resource bundle, that includes the clinical information represented in the document, as FHIR resources within a FHIR document resource.

A computer-readable storage medium encoded with program instructions in accordance with an example aspect is described. The program instructions, when executed by one or more processors, performs a computer-implemented method. The method includes receiving a document that includes clinical information and that is structured in accordance with a first standard format, and generating an object model document to include at least one information-value pair of a plurality information-value pairs that each comprise an information identifier and an associated value string that are included in the document. The method also includes assigning path definitions for each of the at least one information-value pair that define mappings between the at least one information-value pair in the object model document and objects of an ontology model having a second standard format, and generating an instance model of the ontology model that is representative of the document and that is in the second standard format based on the path definitions. The generating further includes creating objects for the instance model, and providing values to the objects for the instance model corresponding to each of the at least one information-value pair.

In embodiments, the method further includes generating resources in accordance with the second standard format from the objects for the instance model.

In embodiments, in the method, creating objects for the instance model includes creating a number of objects based on a request for information that corresponds to a same number of information-value pairs.

In embodiments, in the method, the first standard format is CCDA and the second standard format is FHIR. In embodiments, the method further includes generating a FHIR resource bundle, that includes the clinical information represented in the document, as FHIR resources within a FHIR document resource. In embodiments, the method still further includes storing the FHIR resource bundle in a database, and providing access to the database to accept queries for specific ones of the FHIR resources.

In embodiments, in the method, the document is one of a plurality of documents in accordance with the first standard format that are stored in a repository, and a first information identifier of a first information-value pair in a first section of the document is the same as a second information identifier of a second information-value pair in a second section of another document in the repository.

In embodiments, in the method, the ontology model comprises an RDF model.

Various example embodiments are described in the following subsections. In particular, example resource generator system embodiments are described, followed by example ontology model embodiments, including RDF implementations. Next, further example embodiments and advantages are described, and subsequently example processing device embodiments are described. Finally, some concluding remarks are provided.

III. Example Resource Generator System Embodiments

As noted above, embodiments for systems and devices may be configured to perform their functions and operations (e.g., methods) in various ways, and it is contemplated herein that in various embodiments, one or more components described and/or shown may not be included and that additional components may be included.

Figure 3:
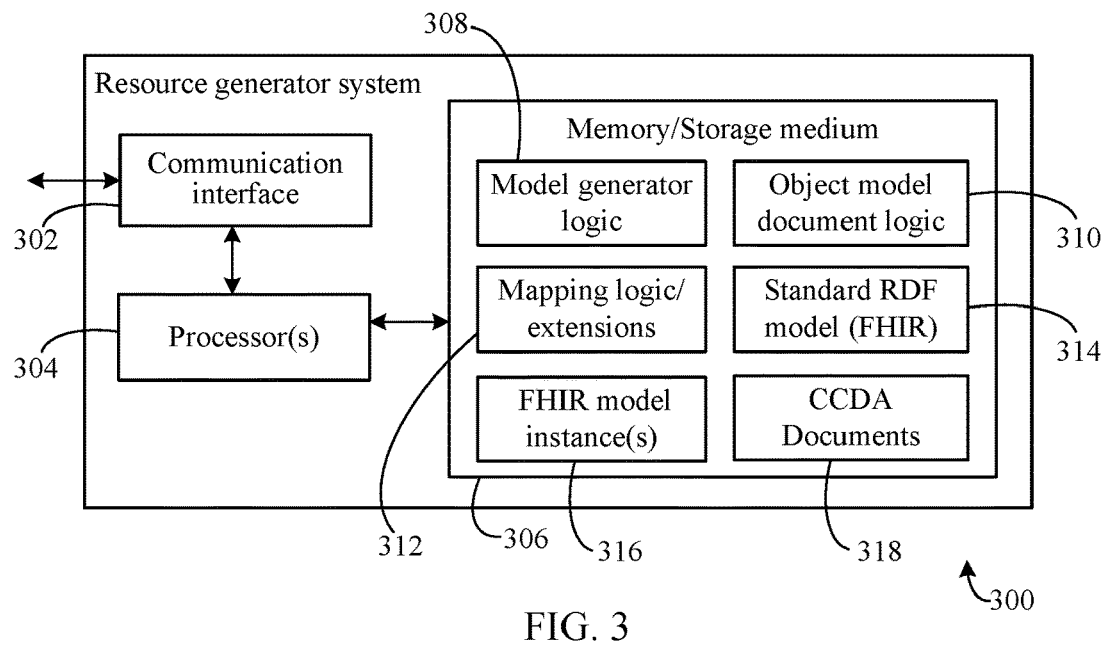
FIG. 3 shows a block diagram of a resource generator system, according to an example embodiment.

Turning now to FIG. 3, a block diagram of a resource generator system 300 is shown, according to an embodiment. Resource generator system 300 may be a further embodiment of resource generator system 104 of FIG. 1 and/or resource generator system 204 of FIG. 2. That is, resource generator system 300 may be included or implemented in a host server, e.g., host server 102 of FIG. 1 and/or host server 202 of FIG. 2, that is communicatively coupled to one or more remote computer systems over a communication link or network, as described above.

Resource generator system 300 includes a communication interface 302, one or more processors ("processor") 304, and a memory/storage medium ("memory") 306. Processor 304 is communicatively coupled to communication interface 302 and to memory 306. Communication interface 302 is configured to be communicatively coupled to a communication link and/or to a network, such as communication link 108 of FIG. 1 and/or network 210 of FIG. 2 for communication with one or more remote devices such as requestors as described herein.

Communication interface 302 may be one or more interfaces, such as hardware network interfaces, that are configured to transmit and/or receive communications and messages, as well as declarations, over a network or communication link as described herein. Processor 304 may be one or more computer processors or processing devices as known to one of skill in the relevant art(s) having the benefit of this disclosure, such as those configured to operate in a computer, a server, a computing systems, and/or the like, as described herein. Processor 304 is configured to execute computer program instructions to perform the described clinical resource generation (e.g., generation of clinical resource information objects) functions and methods.

Memory 306 is a hardware device(s) of, or associated with, a computer, a server, a computing system, and/or the like, as described herein, that is configured to store data/information and/or computer program instructions that may be executed by processor 304. For example, as shown in FIG. 3, memory 306 is configured to store model generator logic 308, object model document logic 310, and mapping logic/extensions 312. Memory 306 is also configured to store a standard RDF model 314 that may be an RDF ontology model in embodiments, one or more of FHR model instances 316, and one or more of CCDA documents 318. In embodiments, one or more of standard RDF model 314, FHR model instances 316, and CCDA documents 318 may not be stored at all times in memory 306, but may be stored upon generation or receipt thereof, as described herein. It is also contemplated herein that, in embodiments, standard RDF model 314 and FHR model instances 316 may respectively be a models based on a framework or data structure implementation other than RDF. Memory 306 is also configured to store object model documents corresponding to CCDA documents with CCDA documents 318.

Figure 4:
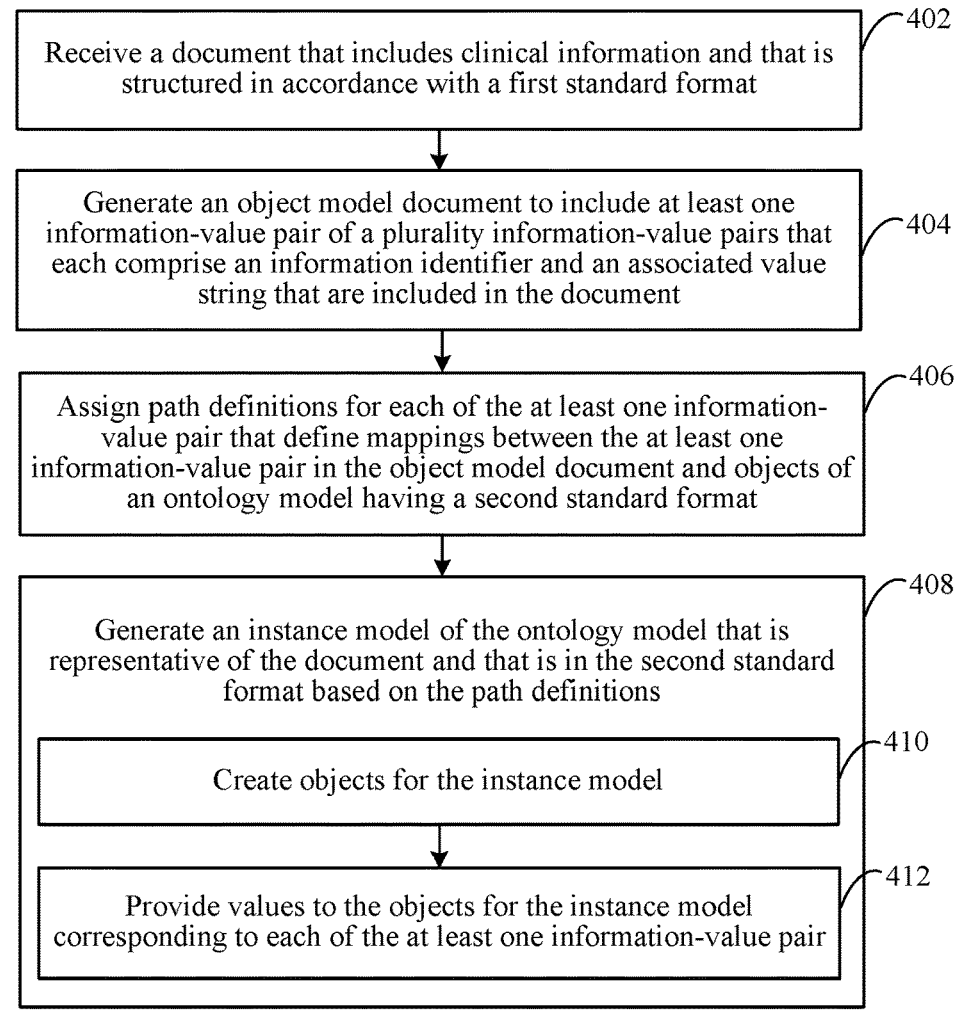
FIG. 4 shows a flowchart of a method for clinical resource generation, according to an example embodiment.

In FIG. 4, a flowchart 400 for clinical resource generation (e.g., generation of clinical resource information objects) is shown, according to an embodiment. That is, flowchart 400 may exemplify a method performed in or by a computing system for clinical resource generation such as FHIR resources. Example techniques and embodiments described herein may be configured and/or implemented to perform various aspects of clinical resource generation according to flowchart 400. For instance, resource generation system 104 of FIG. 1, resource generation system 204 of FIG. 2, and/or resource generation system 300 of FIG. 3, along with any of their respective subcomponents, may perform functions according to flowchart 400 of FIG. 4. Flowchart 400 is described as follows in the context of resource generation system 300 of FIG. 3 for exemplary illustration.

A document that includes clinical information and that is structured in accordance with a first standard format is received (402). For example, a formatted document from a remote computer system (e.g., a requestor such as requestor 206 of FIG. 2) may be received over a network by communication interface 302 of resource generator system 300 in a host provider. The document may be structured/formatted according to CCDA standards in embodiments and as exemplarily illustrated as Example CCDA Document in the preceding Section. Communication interface 302 is configured to provide received documents to processor 304 and/or to memory 306.

Figure 5:
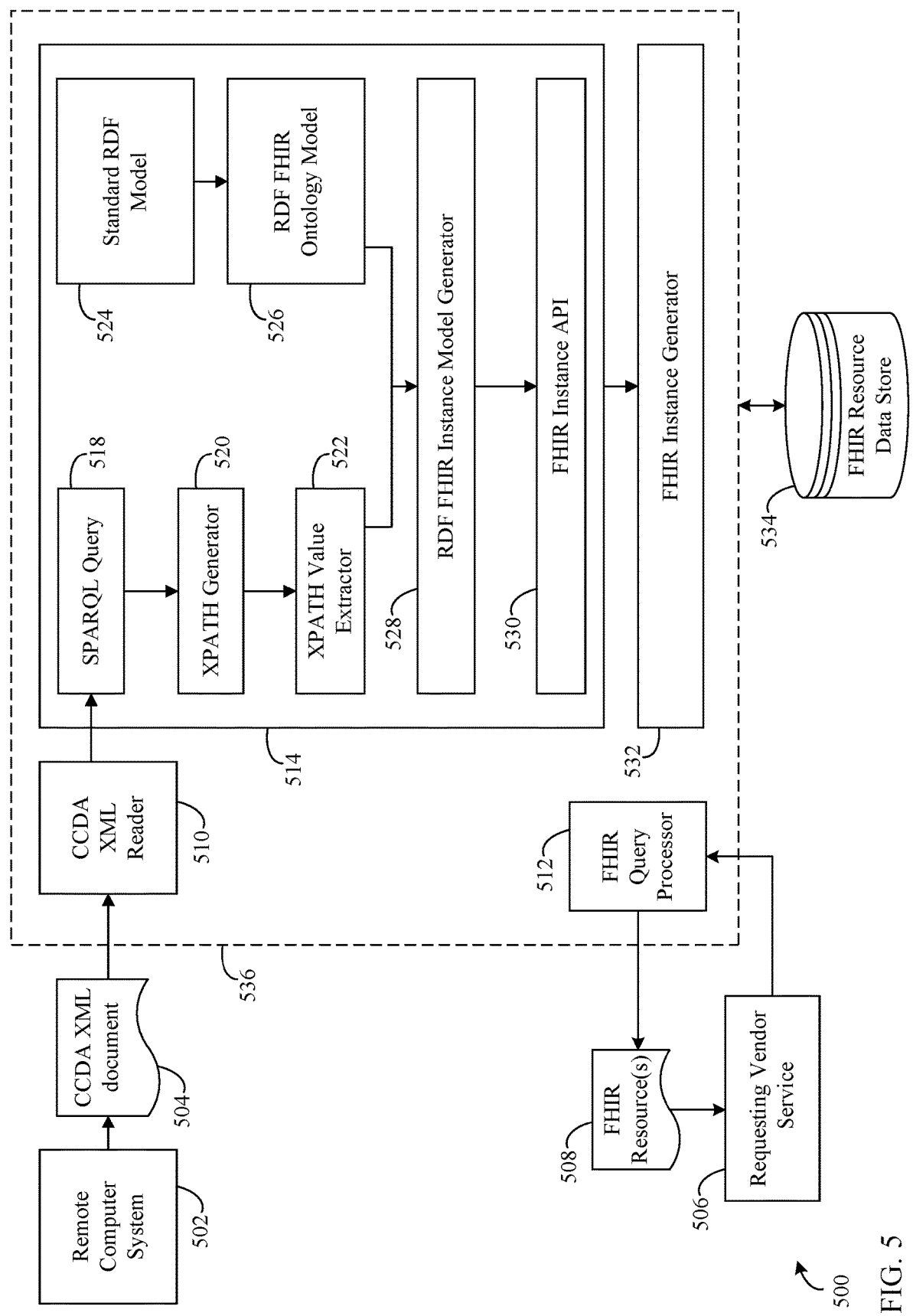
FIG. 5 shows a resource generation system execution flow, according to an example embodiment.

Turning now to FIG. 5, a resource generation system execution flow ("execution flow") 500 is shown, according to an embodiment. Execution flow 500 is described with respect to FIGS. 3 and 4. In embodiments, execution flow 500 may be performed by resource generation system 536 which may be a further embodiment of resource generation system 300 of FIG. 3. As illustrated in execution flow 500, a CCDA XML document ("document") 504 is provided to a CCDA XML reader ("reader") 506 from a remote computer system 502 that may be a further embodiment of a requestor described above in FIGS. 1 and 2 or may be an entity affiliated with a prescriber or health care provider, etc. For instance, communication interface 302 is configured to receive document 504 and to provide document 504 for processing in execution flow 500. As noted, processor 304, described above with respect to FIG. 3, is configured to execute computer program instructions (i.e., computer program logic) stored in memory 306. An execution block 514 is shown in execution flow 500 as representing the execution of computer program instructions for resource generation. Execution block 514 may be executed by processor 304.

Referring back to flowchart 400 of FIG. 4, an object model document is generated to include at least one information-value pair of a plurality information-value pairs that each comprise an information identifier and an associated value string that are included in the document (404). For instance, with respect to execution flow 500 of FIG. 5, when document 504 is received by communication interface 302 and loaded into memory 306 (e.g., as in 402 above), processor 304 may be configured to activate reader 510 from object model document logic 310 when loaded into memory 306 to cause reader 510 to generate the object model document based on document 504. In the Example CCDA Document in the previous Section, an information-value pair for a clinical observation of body weight for the patient is shown: identifier: BODY WEIGHT (MEASURED); value string: "144.84". Reader 510 is configured in this example to generate the object model document to include this information-value pair, as well as information-value pairs for the given name and the family name of the patient: given, "Paulina"; family: "Coffin".

Flowchart 400 continues with path definitions being assigned for each of the at least one information-value pair that define mappings between the at least one information-value pair in the object model document and objects of an ontology model having a second standard format (406). For instance, processor 304 is configured to load into memory 306, and activate, mapping logic of mapping logic/extensions 312 to cause the assignment of path definitions for each information-value pair. A base RDF model, e.g., standard RDF model 314, is loaded into memory 306 as shown in a standard RDF model 524 in execution block 514, and is augmented with defined mappings and/or a model of extension classes, e.g., from mapping logic/extensions 312, also loaded into memory 306, for defining the available mappings between the information-value pairs in the object model document and objects of standard RDF model 314 in a second standard format (in embodiments, standard RDF model 314 is a FHIR model). The augmented model having the class extensions and/or defined mappings is shown in execution block 514 an RDF FHIR ontology model 526. In some embodiments, RDF models and extensions as described herein may be implemented according to the "OWL" Web Ontology Language (see https://www.w3.org/TR/owl-ref/), and/or equivalents.

SPARQL, a recursive acronym identifying the SPARQL Protocol and RDF Query Language, may be utilized in embodiments for XPATH generation. The mapping logic of mapping logic/extensions 312 assigns the path definitions such as XPATH definitions between each information-value pairs of the object model document and the appropriate, available object of the augmented RDF model by first querying RDF FHIR ontology model 526 using SPARQL query logic 518 which may be included in mapping logic/extensions 312, although other query protocols are contemplated herein. SPARQL query logic 518 is configured to provide queries against models, according to embodiments, such as RDF ontology models as described herein. That is, in embodiments, SPARQL query logic 518 is configured to query the augmented RDF model, RDF FHIR ontology model 526, for defined mappings of the standard model components and properties (including, e.g., "child" properties to which the actual values, i.e., codings, are mapped in the FHIR model ("CodeableConcept.coding"), which may then have objects generated therefrom, e.g., Java™ objects, that are provided to XPATH generator logic 520.

XPATH generator logic 520 may also be included in mapping logic/extensions 312. XPATH generator logic 520 is configured to generate the paths between each model component of RDF FHIR ontology model 526 and the information-value pairs of the object model document by linking the mappings of the model components and properties with CCDA codes (such as but not limited to Logical Observation Identifiers Names and Codes ("LOINC" ®)) of the information-value pairs. In the Example CCDA Document above, the BODY WEIGHT (MEASURED) identifier is associated with LOINC code "3141-9" which is in turn associated with a LOINC code of 8716-3 for "Vital signs," and so on. XPATH generator logic 520 links the LOINC code "3141-9" for BODY WEIGHT (MEASURED) with the appropriate defined mapping for clinical observations in RDF FHIR ontology model 526.

Continuing with this example, the value property ("Val") may be given as "/entry/organizer/component/observation/code." This is interpreted by the executing logic such that for observation entries in a CCDA Vital Signs section (when identified in the CCDA by LOINC "8716-3"), the code for each included observation can be found by following the XPATH "/entry/organizer/component/observation/code" (i.e., the value in Val). Furthermore, the CCDA entry specifies that the actual code value relates to the Observation.code property of the FHIR Observation resource. These are the "parent" class and the "parent" property in which the code should be placed within the FHIR model, as described herein. It should also be noted that FHIR model components and properties for clinical observations are not a simple strings (i.e., the code value). Rather, the Observation.code is another FHIR datatype object called CodeableConcept. A CodeableConcept consists of a Coding (another FHIR datatype) and a text (string) property. Ultimately, the code for an observation from the CCDA becomes the value of the Coding.code property of an object that is referenced by a CodeableConcept.coding property in a FHIR model instance, which is referenced by an Observation.code property. As an illustrative, non-limiting example, a FHIR Coding object "A" is created whereby A.code=3141-9, and A.display=BODY WEIGHT (MEASURED). Moreover, a FHIR CodeableConcept object "B" is created, whereby B.coding=A (i.e., the Coding object). Finally, a FHIR Observation object "C" is created, which among other things has its coding property set to B (i.e., C.coding=B). Example XPATH definitions according to the above examples may be:

```
. . .
, [P:Observation] [PProp:Observation.code]
 [PVal:/entry/organizer/component/observation/code]
 [CProp:CodeableConcept.coding]
    [Val:/entry/organizer/component/observation/code]
    [Assoc:[10153-2, 10155-0, 10157-2, 11384-5, 11450-4, 11496-7,
    11502-2, 29762-2, 30954-2, 48765-2, 8716-3]]
. . .
, [P:Composition] [PProp:Composition.subject]
    [PVal:/recordTarget/patientRole] [CProp:Patient.name]
    [Val:/patient/name]
, [P:Patient] [PProp:Patient.name] [PVal:/patient/name]
    [CProp:HumanName.family] [Val:/family]
, [P:Patient] [PProp:Patient.name] [PVal:/patient/name]
    [CProp:HumanName.given] [Val:/given]
, [P:HumanName] [PProp:HumanName.family] [PVal:/family]
    [Val:/family]
, [P:HumanName] [PProp:HumanName.given] [PVal:/given] [Val:/given]
. . .
```

Next, XPATH value extractor logic 522, which may be included in mapping logic/extensions 312, is configured to utilize the XPATH definitions to create the explicit maps that relate a value of an information-value pair in a CCDA document to the property in the FHIR model to which the value is associated. Because various sections of a CCDA document, all containing observations, can be organized by different structures, it is necessary to assemble all XPATHs in which an Observation may occur. For example, an Observation in one section of a CCDA may be contained within organizer/composition components, but in another section be contained in act/entryRelationship components, and in yet other sections, neither. Hence, the embodiments described herein provide for coverage of all the structures in a CCDA document within which an Observation may occur. Accordingly, XPATH value extractor logic 522 is configured to create the explicit maps by iteratively assembling all possible XPATH definitions.

XPATH value extractor logic 522 is configured to utilize the explicit maps to take the CCDA code for weight, and store it in a FHIR Coding object (Coding.code) property using 'breadcrumb' information, as shown below. Further, if read in reverse order, the constructed map provides that this Coding object is referenced by a CodeableConcept (via the CodeableConcept.coding), which is in turn referenced by an Observation (via Observation.code), which is one of (i.e., referenced by) the entries in a particular section (via SectionComponent.entry). Therefore, the CCDA construction of:

--- ns:section/ns:entry/ns:organizer/ns:component/ns:observation/ns:code
/@code [CCDA code value],

--- is mapped to FHIR as:

---

SectionComponent.entry => Observation.code =>
CodeableConcept.coding => Coding.code,

--- according to:

---

[P:SectionComponent] [PProp:SectionComponent.entry] [PVal:section]
 [CProp:Coding.code]
 [Val:ns:section/ns:entry/ns:organizer/ns:component/ns:observation/
 ns:code/@code] [Res:observation] [Assoc:[10153-2, 10155-0,
 10157-2, 11384-5, 11450-4, 11496-7, 11502-2, 29762-2, 30954-2,
 48765-2, 8716-3]] [Bread:[SectionComponent=
 SectionComponent.entry, Observation=Observation.code,
 CodeableConcept=CodeableConcept.coding, Coding=Coding.code]].

---

Accordingly, XPATH value extractor logic 522 is configured to extract the values of the information-value pairs of the CCDA document, document 504.

Continuing with flowchart 400 of FIG. 4, an instance model, of the RDF ontology model, that is representative of the document and that is in the second standard format based on the path definitions is generated (408). For example, RDF FHIR instance model generator logic ("instance model generator logic") 528 which may be a part of model generator logic 308 of FIG. 3, is configured to generate an RDF FHIR instance model representative of the CCDA document, document 504 (although other formats in addition to FHIR are contemplated herein). In embodiments, the FHIR instance model may be stored in memory 306 of FIG. 3 as FHIR model instance(s) 316. Instance model generator logic 528 is configured to dynamically assemble the RDF FHIR instance model based on RDF FHIR ontology model 526, and the XPATH mapping and the values from (406). According to some embodiments, for one or more, or each, value extracted from document 504, as described above, instance model generator logic 528 is configured to assemble a number of corresponding FHIR objects that will be associated with the CCDA values. That is, instance model generator logic 528 assembles the RDF FHIR instance model to generate a specific FHIR instance that corresponds to the values for patient and clinical information, such as but not limited to observations, included in document 504.

For example, objects for the instance model are created (410), and values are provided to the objects for the instance model corresponding to each of the at least one information-value pair (412) by instance model generator logic 528. Instance model generator logic 528 is configured to create instance model objects, e.g., for the FHIR instance model, based on standard RDF FHIR model 314 and the XPATH mapping described above. Standard RDF FHIR model 314 includes a standard resource kind having objects for each of Observation and Patient, in addition to others, as would be apparent to those of skill in the relevant art(s) having the benefit of this disclosure. In the Example CCDA Document discussed herein, a single observation of body weight measured for a patient is shown. Accordingly, a FHIR object for the patient and a FHIR object for the observation would be assembled from standard RDF FHIR model 314 for the for the FHIR instance model based on the XPATH mapping, while other standard FHIR objects may be excluded from the assembly of the FHIR instance model.

In examples where two observations are included for a patient in a CCDA document, two instances of the FHIR observation object of the RDF FHIR model 314 would be used to assemble the FHIR instance model, likewise for three or more observations, as well as for other types of FHIR resources and their objects. In this manner, RDF FHIR model 314 serves as a standard template that is utilized for any number of a given FHIR resource that is required for generating objects in a FHIR instance model.

It should also be noted that in embodiments, the specific FHIR instance may include only resources and objects that correspond to the information present in document 504 for which the specific FHIR instance is representative, and/or may include a subset of resources and objects that is less than all of the resources and objects in the standard FHIR model.

In providing values or codings to the objects for the FHIR instance model that correspond to each information-value pair(s) of the CCDA document, e.g., document 504, the values of the information-value pairs extracted by XPATH value extractor logic 522 based on the XPATH mappings, as described above, are assigned to the corresponding objects in the FHIR instance model by instance model generator logic 528. Values/codings may be assigned as objects are assembled for the FHIR instance model or subsequent to the assembly.

Figure 6:
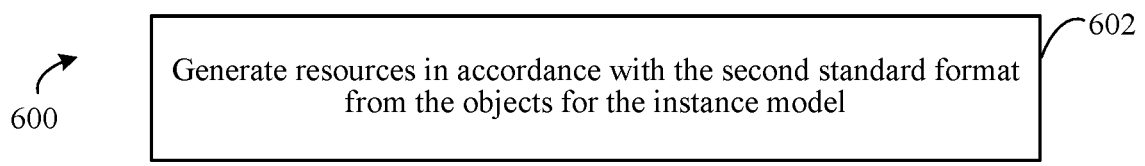
FIG. 6 shows a flowchart of a method for clinical resource generation, according to an example embodiment.

In FIG. 6, a flowchart 600 for clinical resource generation (e.g., generation of clinical resource information objects) is shown, according to an embodiment. That is, flowchart 600 may exemplify a method performed in or by a computing system for clinical resource generation such as FHIR resources. Example techniques and embodiments described herein may be configured and/or implemented to perform various aspects of clinical resource generation according to flowchart 600. For instance, resource generation system 104 of FIG. 1, resource generation system 204 of FIG. 2, and/or resource generation system 300 of FIG. 3, along with any of their respective subcomponents, may perform functions according to flowchart 600 of FIG. 6. Flowchart 600 is described as follows in the context of resource generation system 300 of FIG. 3 and execution flow 500 of FIG. 5 for exemplary illustration.

Resources are generated in accordance with the second standard format from the objects for the instance model (602). For example, the FHIR instance model generated based on the CCDA document (e.g., document 504 having a first format, CCDA) in (408) by instance model generator logic 528 has a FHIR standard format, e.g., the second format, although other standard formats are contemplated herein. As noted above, generated FHIR instance models may be stored in memory 306 of FIG. 3 as FHIR model instance(s) 316. A FHIR instance model generated, or generated and stored, is provided by a FHIR instance application programming interface ("API") 530 to FHIR instance generator logic 532 which is configured to extract one or more instance values/definitions from FHIR instance models to generate individual FHIR resource objects.

These generated FHIR resource objects may be stored in a FHIR resource data store 534. FHIR resource data store 534 may comprise, e.g., one or more databases, and may be a central or distributed data store. FHIR resource data store 534 may be hosted by a service provider of a resource generation system as described herein, or may be hosted by a third-party provider that grants access to FHIR resource data store 534 for such resource generation systems. FHIR resource data store 534 may be a part of a resource generation system such as resource generation system 300 of FIG. 3 or resource generation system 536 of FIG. 5, or may be a separate component(s) that are accessible by resource generation systems described herein over a network or other communication connection.

Additionally, generated FHIR resource objects may be stored in FHIR resource data store 534 as groups based on a patient. For example, when more than one FHIR resource objects are generated, as described herein, and stored in FHIR resource data store 534, the FHIR resource objects may be grouped, tagged, indexed, etc., according to the patient associated therewith. In such embodiments, access efficiency for these FHIR resource objects may be increased. As another example, newly-generated FHIR resource objects may be added to groups of existing, previously-generated FHIR resource objects stored in FHIR resource data store 534 based on commonality, such as but without limitation, a given patient.

In embodiments, a FHIR instance model and/or FHIR resource objects may be generated responsive to a request or query. It is also contemplated herein that some such requests or queries may specify a number of observations, values, or other information for a FHIR instance model that is less than the total number of observations, values, or other information contained in the CCDA document. FHIR instance models generated, or generated and stored, that are provided by API 530 to FHIR instance generator logic 532 as noted above in (602), may be provided based on a request or a query.

Figure 7:
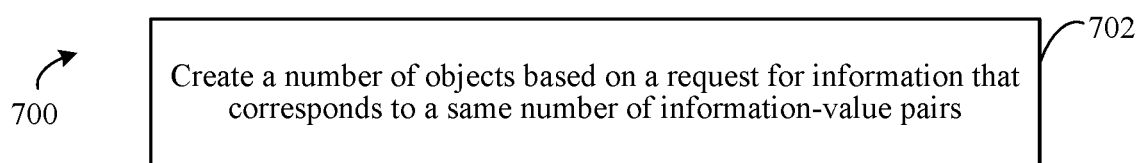
FIG. 7 shows a flowchart of a method for clinical resource generation, according to an example embodiment.

In FIG. 7, a flowchart 700 for clinical resource generation (e.g., generation of clinical resource information objects) is shown, according to an embodiment. That is, flowchart 700 may exemplify a method performed in or by a computing system for clinical resource generation such as FHIR resources. Example techniques and embodiments described herein may be configured and/or implemented to perform various aspects of clinical resource generation according to flowchart 700. For instance, resource generation system 104 of FIG. 1, resource generation system 204 of FIG. 2, and/or resource generation system 300 of FIG. 3, along with any of their respective subcomponents, may perform functions according to flowchart 700 of FIG. 7. Flowchart 700 is described as follows in the context of resource generation system 300 of FIG. 3 and execution flow 500 of FIG. 5 for exemplary illustration.

A number of objects are created based on a request for information that corresponds to a same number of information-value pairs (702). For instance, referring also to execution flow 500 of FIG. 5, a requesting vendor service 506 may request specific clinical information in the FHIR standard format from, or may query, a FHIR query processor 512. Requesting vendor service 506 may request/query for any number of clinical information items associated with information-value pairs of a patient CCDA document. Requesting vendor service 506 may comprise computing devices of various vendor services seeking clinical information of patients, and in embodiments, may comprise computing devices of a trading partner(s), a doctor or doctor's office (including nurses and/or other staff), a pharmacy, a health care provider(s), and/or another third-party entity(ies). In some cases, a request/query may be generated by a service provider of a resource generator system, e.g., in order to build a library of FHIR resources for patients. FHIR query processor 512 may be a separate processor of a resource generator system as described herein, e.g., resource generator system 300 of FIG. 3 or resource generator system 536 of FIG. 5, or may be a program or application executing on a processor(s) of a resource generation system.

In embodiments, a request/query received from requesting vendor service 506 by a resource generator system may be received via a communication interface as described herein. When provided to FHIR query processor 512, a received request may cause FHIR query processor 512 to activate and perform FHIR query functions.

For instance, in embodiments, responsive to a received request/query FHIR query processor 512 may be configured to query FHIR resource data store 534 for at least one FHIR resource associated with clinical information for a given patient as included in the request/query from requesting vendor service 506. For FHIR resources associated with the requested clinical information, FHIR query processor 512 is configured to receive query results for the FHIR resources and provide at least one FHIR resource 508 to requesting vendor service 506.

In some embodiments, such as when a query of FHIR resource data store 534 does not return valid results associated with the request/query, FHIR query processor 512 may be configured to cause activation of reader 510 which in turn is configured to determine if any CCDA documents of the patient in the request that are stored in CCDA documents 318 contain one or more items of the clinical information requested. In such cases, a FHIR instance model and/or FHIR resource objects for the determined CCDA document(s) may be automatically generated as described herein, such as but not limited to, with respect to flowchart 400 of FIG. 4, flowchart 600 of FIG. 6, and/or flowchart 700 of FIG. 7.

Likewise, in embodiments where a CCDA document is included in a request/query for patient clinical information received from requesting vendor service 506, FHIR query processor 512 may be configured to cause activation of reader 510, and a FHIR instance model and/or FHIR resource objects for the determined CCDA document(s) may be automatically generated as described herein, such as but not limited to, with respect to flowchart 400 of FIG. 4, flowchart 600 of FIG. 6, and/or flowchart 700 of FIG. 7.

Figure 8:
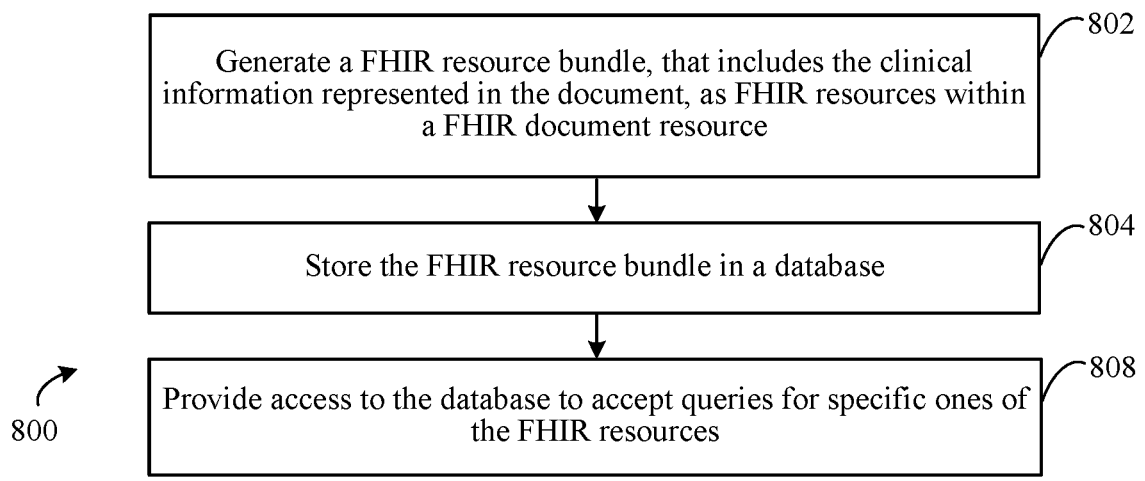
FIG. 8 shows a flowchart of a method for clinical resource generation, according to an example embodiment.

In FIG. 8, a flowchart 800 for clinical resource generation (e.g., generation of clinical resource information objects) is shown, according to an embodiment. That is, flowchart 800 may exemplify a method performed in or by a computing system for clinical resource generation such as FHIR resources. Example techniques and embodiments described herein may be configured and/or implemented to perform various aspects of clinical resource generation according to flowchart 800. For instance, resource generation system 104 of FIG. 1, resource generation system 204 of FIG. 2, and/or resource generation system 300 of FIG. 3, along with any of their respective subcomponents, may perform functions according to flowchart 800 of FIG. 8. Flowchart 800 is described as follows in the context of resource generation system 300 of FIG. 3 and execution flow 500 of FIG. 5 for exemplary illustration.

A FHIR resource bundle, that includes the clinical information represented in the document, as FHIR resources within a FHIR document resource is generated (802). For instance, as noted above in (602) of flowchart 600, FHIR resources (e.g., resources in accordance with the second standard format) from the objects for the instance model are generated, in embodiments. These FHIR resources generated by FHIR instance generator logic 532 may be grouped by FHIR instance generator logic 532 as a FHIR resource bundle. The FHIR resource bundle may be a FHIR document resource comprised of the FHIR resources generated by FHIR instance generator logic 532. For example, one or more generated FHIR resource objects may be provided in a formatted document according to XML or JavaScript Object Notation (JSON) formats, and/or the like.

The FHIR resource bundle is stored in a database (804). The FHIR resource bundle generated in (802) may be stored in FHIR resource data store 534, according to embodiments. For example, FHIR instance generator logic 532 may be configured to store the FHIR resource bundle generated in (802) in FHIR resource data store 534 subsequent to its generation.

Access to the database is provided to accept queries for specific ones of the FHIR resources (806). For example, a resource generation system as described herein and as noted above, such as resource generator system 300 of FIG. 3 or resource generator system 536 of FIG. 5, may be configured to access FHIR resource data store 534 for storing and querying of FHIR resources and/or FHIR resource bundles. FHIR resource data store 534 is thus configured to provide access to resource generator systems for the FHIR resources and/or FHIR resource bundles stored therein responsive to requests/queries for clinical information related to patients. Access for requests/queries may also be provided to insurance providers, doctors/prescribers, pharmacists, pharmacy benefits management (PBM) entities, and/or other types of health care providers, in some embodiments.

In embodiments, the FHIR resource bundles may be generated responsive to a request/query as in the description above with respect to (702) of flowchart 700. For instance, responsive to a request/query, FHIR query processor 512 may cause a FHIR instance model representative of a CCDA document to be generated from which a FHIR document resource may be generated and then queried for a FHIR resource bundle.

IV. Example Ontology Model Embodiments

As described above, resource generation systems may be configured in various ways to perform their described functions. For instance, resource generation systems may be configured to generate FHIR resources for clinical information (e.g., that is contained in CCDA documents) for patients where the information is associated with, but not limited to, patient identification, practitioners, appointments, clinical observations, clinical documents, medications, accounts, and/or the like, as defined by the FHIR standard. An extensive list of resources for FHIR is not provided here for the sake of brevity, however, it is contemplated that any FHIR resources may be similarly or analogously treated and/or modeled according to the examples described herein.

Modeling based on metadata that defines the structure and properties of FHIR resources in RDF may be performed according to the described techniques and embodiments. The RDF modeling allows the described embodiments to generate FHIR instance models using desired information from CCDA documents and mappings to standard RDF models, as these models are structured to provide for versatile, targeted queries for clinical resource attainment. For example, a "Patient" resource for FHIR may be modeled based on its metadata to allow the generation of an RDF model for the resource that includes dependent resources such as, but without limitation, vital signs and body weight. The following is an example, non-limiting code segment represented in ".ttl" format, e.g., in a terse RDF triple language ("TTL"), showing a compact text form of a graphical RDF model:

```
@prefix CCDA:  <http://hostProvider.org/CCDA#> .
@prefix rdf:   <http://www.w3.org/1999/02/22-rdf-syntax-ns#> .
@prefix owl:   <http://www.w3.org/2002/07/owl#> .
@prefix HostProviderFHIR:
<http: //hostProvider.org/HostProviderFHIR#> .
@prefix xsd: <http://www.w3.org/2001/XMLSchema#> .
@prefix rdfs: <http://www.w3.org/2000/01/rdf-schema#> .
CCDA:Observation_1f20e739-e1db-49b3-ba0b-3ff1982dd765
        a       <http://hostProvider.org/FHIR#Observation> ;
        <http://hostProvider.org/FHIR#Observation.code>
                CCDA:CodeableConcept_1d48f00c-f444-40ae-8a1e-
fde07a054010 .
CCDA:CodeableConcept_1d48f00c-f444-40ae-8a1e-fde07a054010
        a       <http://hostProvider.org/FHIR#CodeableConcept> ;
        <http://hostProvider.org/FHIR#CodeableConcept.coding>
                CCDA:Coding_87fb56c3-cf55-4a42-b49e-4df7e7ad772e .
CCDA:Coding_87fb56c3-cf55-4a42-b49e-4df7e7ad772e
        a       HostProviderFHIR:Coding ;
        <http://hostProvider.org/FHIR#Coding.code>
                "3141-9" ;
        <http://hostProvider.org/FHIR#Coding.display>
                "BODY WEIGHT (MEASURED)" .
CCDA:Patient_758af88b-d467-45f4-9907-56896e5480f4
        a       <http://hostProvider.org/FHIR#Patient> ;
        <http://hostProvider.org/FHIR#Patient.name>
                CCDA:HumanName_e31bbafd-165c-4a88-8f8c-
684e2e5cafe1 .
<http://hostProvider.org/CCDA>
        a                       owl:Ontology ;
        owl:imports
<http://hostProvider.org/HostProviderFHIR> ;
        owl:versionInfo    "Auto Generated from Profile" .
CCDA:SectionComponent_5a90c841-125e-4c83-84ab-bb6275df4987
        a       <http://hostProvider.org/FHIR#SectionComponent> ;
        <http://hostProvider.org/FHIR#SectionComponent.code>
                CCDA:CodeableConcept_11acfede-4fa2-4f6e-87e8-
38526a4a7645 ;
        <http://hostProvider.org/FHIR#SectionComponent.entry>
                CCDA:List_ef1b12ea-5764-49d8-998c-af9af9c9825d ;
        <http://hostProvider.org/FHIR#SectionComponent.title>
                "Vital Signs" .
CCDA:CodeableConcept_11acfede-4fa2-4f6e-87e8-38526a4a7645
        a       <http://hostProvider.org/FHIR#CodeableConcept> ;
        <http://hostProvider.org/FHIR#CodeableConcept.coding>
                CCDA:Coding_38ca1604-9ddb-41d4-8239-
76ca2f6abab1 .
```

-continued

```
CCDA:Coding_38ca1604-9ddb-41d4-8239-76ca2f6abab1
    a       HostProviderFHIR:Coding ;
        <http://hostProvider.org/FHIR#Coding.code>
            "8716-3" .
CCDA:BundleEntryComponent_0c50e01c-d979-48fb-a94c-bf2801e5bb7b
    a
    <http://hostProvider.org/FHIR#BundleEntryComponent> ;
    <http://hostProvider.org/FHIR#BundleEntryComponent.resource>
            CCDA:Composition_8cfd1b14-0aac-478e-af60-
a234ace090da .
CCDA:ListEntryComponent_3386df8e-3610-4278-8e03-2b7f7b59178a
    a       <http://hostProvider.org/FHIR#ListEntryComponent>
;
        <http://hostProvider.org/FHIR#ListEntryComponent.item>
            CCDA:Observation_1f20e739-e1db-49b3-ba0b-
3ff1982dd765 .
CCDA:List_ef1b12ea-5764-49d8-998c-af9af9c9825d
    a       <http://hostProvider.org/FHIR#List> ;
    <http://hostProvider.org/FHIR#List.entry>
            CCDA:ListEntryComponent_3386df8e-3610-4278-8e03-
2b7f7b59178a ;
        <http://hostProvider.org/FHIR#List.mode>
            "working" ;
        <http://hostProvider.org/FHIR#List.status>
            "current" .
CCDA:HumanName_e31bbafd-165c-4a88-8f8c-684e2e5cafe1
    a       <http://hostProvider.org/FHIR#HumanName> ;
    <http://hostProvider.org/FHIR#HumanName.family>
            "Coffin" ;
    <http://hostProvider.org/FHIR#HumanName.given>
            "Paulina " .
CCDA:Bundle_c0e548fd-2145-4ef4-a227-286d4be52a5f
    a       <http://hostProvider.org/FHIR#Bundle> ;
    <http://hostProvider.org/FHIR#Bundle.entry>
            CCDA:BundleEntryComponent_0c50e01c-d979-48fb-
a94c-bf2801e5bb7b .
CCDA:Composition_8cfd1b14-0aac-478e-af60-a234ace090da
    a       <http://hostProvider.org/FHIR#Composition> ;
    <http://hostProvider.org/FHIR#Composition.section>
            CCDA:SectionComponent_5a90c841-125e-4c83-84ab-
bb6275df4987 ;
        <http://hostProvider.org/FHIR#Composition.subject>
            CCDA:Patient_758af88b-d467-45f4-9907-56896e5480f4
.
...
```

The TTL code portion example shown above is illustrative in nature, and is not to be considered limiting. It is contemplated herein that other types of modeling and model representation may be used, as would be understood by a person of skill in the relevant art(s) having the benefit of this disclosure. In embodiments, RDF ontology models may be implemented according to the "OWL" Web Ontology Language (see https://www.w3.org/TR/owl-ref/), and/or their equivalents.

As noted, resource generator system 104 of FIG. 1, along with further example embodiments thereof as described herein, is configured to automatically generate an ontology model (e.g., through RDF) of a FHIR model instance based on information in a CCDA document(s) and a standard RDF FHIR model using mappings therebetween. The standard RDF FHIR model is a uniform model for the FHIR standard and the instance model may include one or more of any element of the standard RDF FHIR model based on the presence of one or more information-value pairs in the CCDA document that correspond to the FHIR element.

Figure 9:
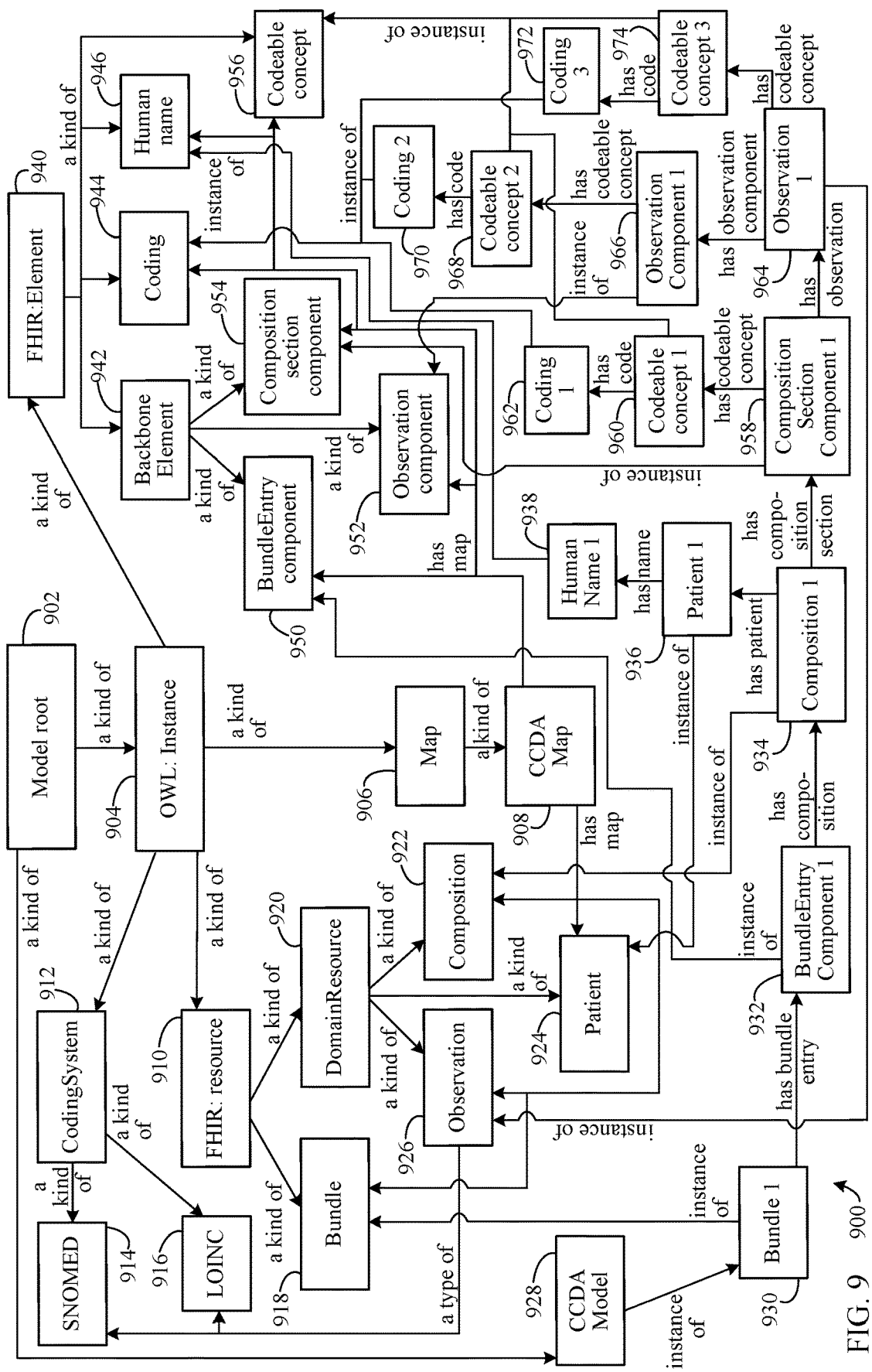
FIG. 9 shows an ontology model, according to an example embodiment.

In FIG. 9, an ontology model 900 is shown, according to an embodiment. Ontology model 900 is a non-limiting, example ontology model embodiment that is illustrative in the context of the Example CCDA Document described above. In embodiments, ontology model 900 may correspond to an FHIR instance model representative of the Example CCDA Document.

Ontology model 900 includes a hierarchical structure of dependencies and attributes based on a root instance model root 902. Ontology model 900 is illustrated with respect to OWL according to an embodiment. From model root 902, an OWL: Instance 904 depends, which has "a kind of" attribute of model root 902. Ontology model 900 also includes a CCDA model 928 that depends from model root 902 and has "a kind of" attribute of model root 902.

From OWL: Instance 904, a Map element 906, a FHIR: resource element 910, a CodingSystem element 912, and a FHIR: Element 940 depend, each of which are "a kind of" OWL: Instance 904. A Systematized Nomenclature of Medicine (SNOMED) element 914 and a LOINC element 916 depend from CodingSystem element 912 and are "a kind of" CodingSystem element 912. From FHIR: resource element 910 a Bundle element 918 and a DomainResource 920 depend and are "a kind of" FHIR: resource element 910. A Bundle 1 930 is "an instance of" both CCDA Model 928 and Bundle element 918, and "has bundle entry" BundleEntry Component 1 932. From Map element 906, a CCDA Map element 908 depends that is "a kind of" Map element 906. Bundle element 918 includes a "has map" attribute of CCDA Map element 908.

An Observation element 926, a Composition element 922, and a Patient element 924 each depend from, and are "a kind of," DomainResource 920. Observation element 926, Composition element 922, and Patient element 924 each include a "has map" attribute of CCDA Map element 908, and Observation element 926 is "a type of" SNOMED element 914 and/or LOINC element 916.

From FHIR: Element 940, a Backbone element 942, a Coding element 944, a Human name element 946, and a Codeable concept element 956 depend, each of which are "a kind of" FHIR: Element 940. Coding element 944, Human name element 946, and Codeable concept element 956 each include a "has map" attribute of CCDA Map element 908. A BundleEntry Component element 950, an Observation component element 952, and a Composition section component element 954 depend from, and are each "a kind of," Backbone element 942, and each include a "has map" attribute of CCDA Map element 908.

BundleEntry Component 1 932 is an "instance of" BundleEntry component 950 and "has composition" Composition 1 934 which is an "instance of" Composition 1 element 922. Composition 1 element 922 "has patient" Patient 1 element 936 which is an "instance of" Patient element 924 and "has name" Human name 1 element 938. Human name 1 element 938 is an "instance of" Human name element 946. Composition 1 element 922 "has composition section" Composition section component 1 element 958 which is an "instance of" Composition section component element 954, "has codeable concept" Codeable concept 1 element 960, and "has observation" Observation 1 element 964. Codeable concept 1 element 960 "has code" Coding 1 element 962 which is an "instance of" Codeable concept element 956. Observation 1 element 964 is an "instance of" Observation element 926, "has observation component" Observation component 1 element 966, and "has codeable concept" Codeable concept 3 element 974. Observation component 1 element 966 is an "instance of" Observation component element 952 and "has codeable concept" Codeable concept 2 element 968. Codeable concept 2 element 968 is an "instance of" Codeable concept element 956 and "has code" Coding 2 element 970 which is an "instance of" Coding element 944. Codeable concept 3 element 974 is an "instance of" Codeable concept element 956 and "has code" Coding 3 element 972 which is an "instance of" Coding element 944.

In ontology model 900, with respect to the Example CCDA Document described herein and the body weight observation of a patient, the patient's Human name 1 element may corresponds to "Paulina Coffin," Composition section component 1 element 958 may correspond to "vital signs," and Observation 1 element 964 may correspond to the measured body weight.

V. Further Example Embodiments and Advantages

As noted above, systems and devices, including resource generator systems, may be configured in various ways to automatically generate FHIR resources from CCDA documents. It is also contemplated herein that generation of resources according to the FHIR standard may be performed based on non-CCDA documents, that generation of resources according to non-FHIR standards may be performed based on CCDA documents, and that generation of other non-FHIR standard formats may be performed based on non-CCDA documents.

The described techniques and embodiments provide for the ability to automatically generate specifically tailored FHIR resources for the information in a CCDA document for use cases where only a section, or set, of specific entries from a CCDA document are needed for that use case. For example, automatic generation of specifically tailored FHIR resources for the information in a CCDA document allows for FHIR resources/resource bundles that can be stored in any compliant FHIR repository, with support for responding to FHIR queries, to respond to requests for specific components of CCDA documents with the appropriate set of FHIR resources that answers the query. As a non-limiting, illustrative example, a request/query from a requestor to a resource generation system for patient allergies can be answered by a set of FHIR allergy resources contained in a bundle without any additional and/or undesired information being returned.

The systems and devices herein are configured to consume CCDA documents and generate the document's contents into a general ontological representation using RDF-specified mappings. This representation is then utilized to automatically generate a set of standard FHIR resources that can be stored in a standard FHIR repository.

The described embodiments and techniques can be used to generate FHIR resources and bundles equivalent to CCDA documents, allowing for the sharing of information to a healthcare entity that can consume FHIR resources and bundles, but not CCDA documents. By placing the generated FHIR resources in a FHIR repository, the described embodiments and techniques can also provide access to component information contained in a CCDA document via query, in a well-defined and structured manner.

Additionally, the ease of use for libraries used in implementations of document formatting standards is increased. For example, a specific instance of a FHIR model that corresponds to any information, or any requested information, in a CCDA document may be generated using a standard FHIR RDF model. That is, the generation of FHIR model instances is itself a model-based generation predicated on a standard FHIR RDF model. Thus the described embodiments and techniques provide for a flexible yet robust way to automatically generate a specific instance of a FHIR model that corresponds to any information, or any requested information, in a CCDA document.

The described techniques and embodiments may be utilized as or in any computing device or distributed computer system. The described techniques and embodiments provide value and efficiency benefits for large, and still increasing, networks of hosts, health care providers, and trading partners that desire to exchange clinical information, even those that are not capable of consuming CCDA documents.

The embodiments and techniques disclosed herein provide for a specific arrangement of components for automatically generating FHIR instance models and FHIR resources. That is, the embodiments and techniques disclosed herein relate to a non-conventional and non-generic arrangement of elements in the resource generation process, e.g., the model-based generation of each specific FHIR instance model based on a generated, standard FHIR model), with customized, user-specified elements specific to each use case. That is, after a standard FHIR model is created, a specific FHIR instance model is subsequently created based on the generated, standard model and mappings to CCDA documents.

The embodiments and techniques disclosed herein also provide for improving the technological process of computer-generated FHIR instance models and FHIR resources through the use of specific relationships and mappings that govern the generation of FHIR instance models and FHIR resources based on a generated standard model, rather than human-based implementations that simply involve the use of a computer, to determine instances for any number of sets of any given type of clinical observation. The described embodiments and techniques utilize specific relationships and mappings that allow for the generation of specific FHIR instance models and FHIR resources based on a generated standard model, and such a technique enables the automation of generating specific FHIR instance models and FHIR resources that previously could not be automated in such a manner. That is, human-based approaches do not involve generating an entire standard FHIR model upon which specific instance models that correspond to individual CCDA documents, or subsets of information therein, are generated. Accordingly, the computer-based generation of FHIR instance models and FHIR resources is improved.

Moreover, according to the described embodiments and techniques, any components of resource generator systems and their functions may be caused to be activated for operation/performance thereof based on other operations, functions, actions, and/or the like, including initialization, completion, and/or performance of the, functions, actions, and/or the like.

In some example embodiments, one or more of the operations of the flowcharts described herein may not be performed. Moreover, operations in addition to or in lieu of the operations of the flowcharts described herein may be performed. Further, in some example embodiments, one or more of the operations of the flowcharts described herein may be performed out of order, in an alternate sequence, or partially (or completely) concurrently with each other or with other operations.

The further example embodiments and advantages described in this Section may be applicable to any embodiments disclosed in this Section or in any other Section of this disclosure.

Embodiments and techniques, including methods, described herein may be performed in various ways such as, but not limited to, being implemented by hardware, or hardware combined with one or both of software and firmware.

VI. Example Processing Device Implementations

Resource generator system and device embodiments described herein, such as resource generator system 104 of FIG. 1, resource generator system 204 of FIG. 2, resource generator system 300 of FIG. 3, and/or resource generator system 536 of FIG. 5, along with any respective components/subcomponents and/or further embodiments thereof, and/or any flowcharts, execution flows, further systems, sub-systems, and/or components, including other network-connected devices, disclosed herein may be implemented in hardware (e.g., hardware logic/electrical circuitry), or any combination of hardware with one or both of software (computer program code or instructions configured to be executed in one or more processors or processing devices) and firmware. In embodiments with respect to the example computer implementations in this Section, main memory, memory cards and memory sticks, memory devices, and/or the like may include and or implement the described techniques and embodiments.

Figure 10:
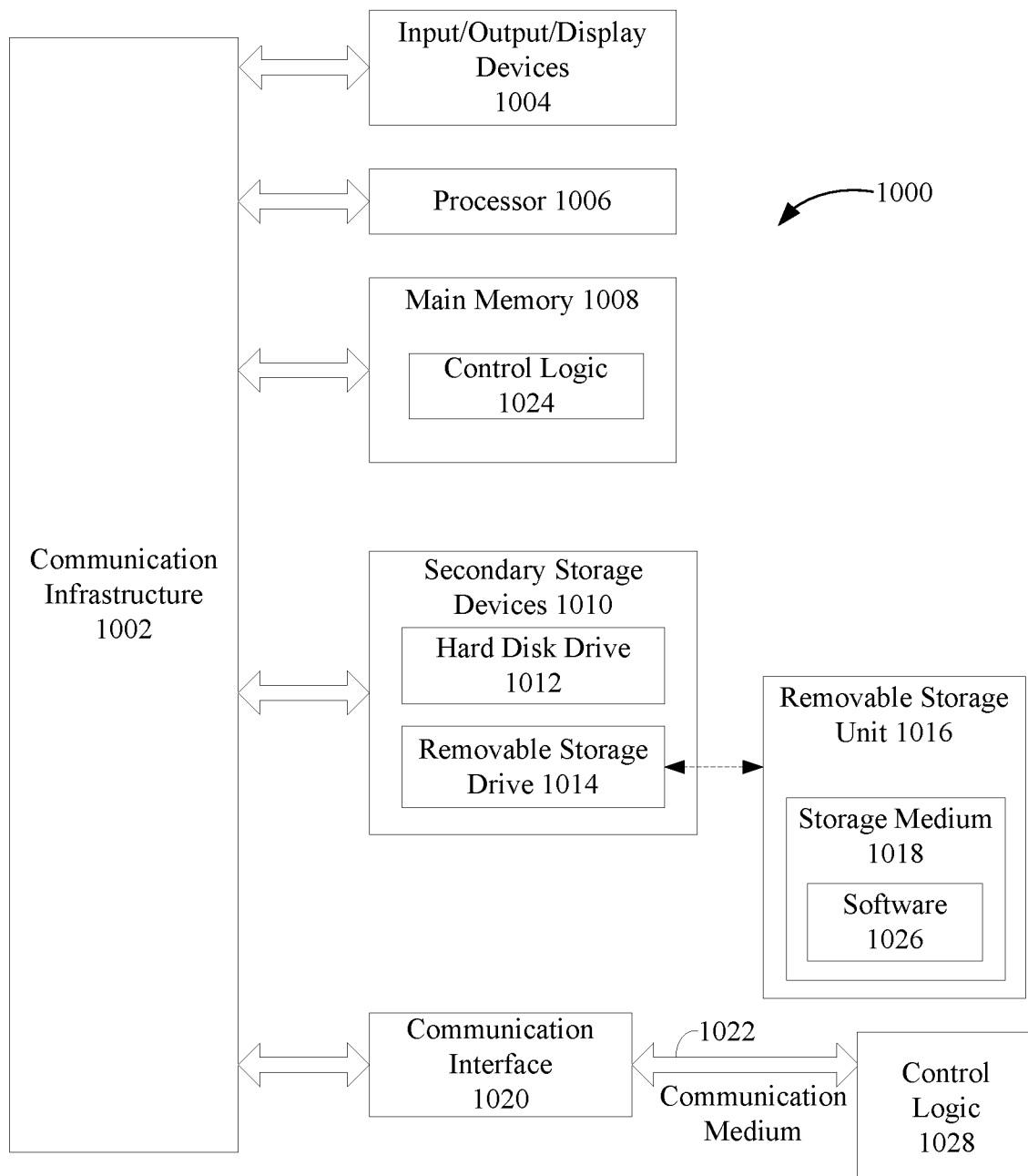
FIG. 10 shows a block diagram of a processing device/system in which the techniques disclosed herein may be performed and the embodiments herein may be utilized.

The embodiments described herein, including devices, systems, methods/processes, and/or apparatuses, may be implemented in or using processing devices, communication systems, servers, and/or, computers, such as a processing device 1000 shown in FIG. 10. It should be noted that processing device 1000 may represent mobile devices, communication devices/systems, entertainment systems/devices, processing devices, and/or traditional computers in one or more embodiments. For example, a resource generation system as described herein, and any of the sub-systems and/or components respectively contained therein and/or associated therewith, along with further embodiments thereof, may be implemented in or using one or more processing devices 1000 and/or similar computing devices.

Processing device 1000 can be any commercially available and well known communication device, processing device, and/or computer capable of performing the functions described herein, such as devices/computers available from International Business Machines®, Apple®, Sun®, HP®, Dell®, Cray®, Samsung®, Nokia®, etc. Processing device 1000 may be any type of computer, including a desktop computer, a server, etc., and may be a computing device or system within another device or system.

Processing device 1000 includes one or more processors (also called central processing units, or CPUs), such as a processor 1006. Processor 1006 is connected to a communication infrastructure 1002, such as a communication bus. In some embodiments, processor 1006 can simultaneously operate multiple computing threads, and in some embodiments, processor 1006 may comprise one or more processors.

Processing device 1000 also includes a primary or main memory 1008, such as random access memory (RAM). Main memory 1008 has stored therein control logic 1024 (computer software), and data.

Processing device 1000 also includes one or more secondary storage devices 1010. Secondary storage devices 1010 include, for example, a hard disk drive 1012 and/or a removable storage device or drive 1014, as well as other types of storage devices, such as memory cards and memory sticks. For instance, processing device 1000 may include an industry standard interface, such a universal serial bus (USB) interface for interfacing with devices such as a memory stick. Removable storage drive 1014 represents a floppy disk drive, a magnetic tape drive, a compact disk drive, an optical storage device, tape backup, etc.

Removable storage drive 1014 interacts with a removable storage unit 1016. Removable storage unit 1016 includes a computer useable or readable storage medium 1018 having stored therein computer software 1026 (control logic) and/or data. Removable storage unit 1016 represents a floppy disk, magnetic tape, compact disk, DVD, optical storage disk, or any other computer data storage device. Removable storage drive 1014 reads from and/or writes to removable storage unit 1016 in a well-known manner.

Processing device 1000 also includes input/output/display devices 1004, such as touchscreens, LED and LCD displays, monitors, keyboards, pointing devices, etc.

Processing device 1000 further includes a communication or network interface 1020. Communication interface 1020 enables processing device 1000 to communicate with remote devices. For example, communication interface 1020 allows processing device 1000 to communicate over communication networks or mediums 1022 (representing a form of a computer useable or readable medium), such as LANs, WANs, the Internet, etc. Network interface 1020 may interface with remote sites or networks via wired or wireless connections.

Control logic 1028 may be transmitted to and from processing device 1000 via the communication medium 1022.

Any apparatus or manufacture comprising a computer useable or readable medium having control logic (software) stored therein is referred to herein as a computer program product or program storage device. This includes, but is not limited to, processing device 1000, main memory 1008, secondary storage devices 1010, and removable storage unit 1016. Such computer program products, having control logic stored therein that, when executed by one or more data processing devices, cause such data processing devices to operate as described herein, represent embodiments.

Techniques, including methods, and embodiments described herein may be implemented by hardware (digital and/or analog) or a combination of hardware with one or both of software and/or firmware. Techniques described herein may be implemented by one or more components. Embodiments may comprise computer program products comprising logic (e.g., in the form of program code or software as well as firmware) stored on any computer useable medium, which may be integrated in or separate from other components. Such program code, when executed by one or more processor circuits, causes a device to operate as described herein. Devices in which embodiments may be implemented may include storage, such as storage drives, memory devices, and further types of physical hardware computer-readable storage media. Examples of such computer-readable storage media include, a hard disk, a removable magnetic disk, a removable optical disk, flash memory cards, digital video disks, random access memories (RAMs), read only memories (ROM), and other types of physical hardware storage media. In greater detail, examples of such computer-readable storage media include, but are not limited to, a hard disk associated with a hard disk drive, a removable magnetic disk, a removable optical disk (e.g., CDROMs, DVDs, etc.), zip disks, tapes, magnetic storage devices, MEMS (micro-electromechanical systems) storage, nanotechnology-based storage devices, flash memory cards, digital video discs, RAM devices, ROM devices, and further types of physical hardware storage media. Such computer-readable storage media may, for example, store computer program logic, e.g., program modules, comprising computer executable instructions that, when executed by one or more processor circuits, provide and/or maintain one or more aspects of functionality described herein with reference to the figures, as well as any and all components, capabilities, and functions therein and/or further embodiments described herein.

Such computer-readable storage media are distinguished from and non-overlapping with communication media (do not include communication media) and modulated data signals. Communication media embodies computer-readable instructions, data structures, program modules or other data in a modulated data signal such as a carrier wave. The term "modulated data signal" means a signal that has one or more of its characteristics set or changed in such a manner as to encode information in the signal. By way of example, and not limitation, communication media includes wireless media such as acoustic, RF, infrared and other wireless media, as well as wired media and signals transmitted over wired media. Embodiments are also directed to such communication media.

The techniques and embodiments described herein may be implemented as, or in, various types of circuits, devices, apparatuses, and systems. For instance, embodiments may be included, without limitation, in processing devices (e.g., illustrated in FIG. 10) such as computers and servers, as well as communication systems such as switches, routers, gateways, and/or the like, communication devices such as smart phones, home electronics, gaming consoles, entertainment devices/systems, etc. A device, as defined herein, is a machine or manufacture as defined by 35 U.S.C. § 101. That is, as used herein, the term "device" refers to a machine or other tangible, manufactured object and excludes software and signals. Devices may include digital circuits, analog circuits, or a combination thereof. Devices may include one or more processor circuits (e.g., central processing units (CPUs), processor 1006 of FIG. 10), microprocessors, digital signal processors (DSPs), and further types of physical hardware processor circuits) and/or may be implemented with any semiconductor technology in a semiconductor material, including one or more of a Bipolar Junction Transistor (BJT), a heterojunction bipolar transistor (HBT), a metal oxide field effect transistor (MOSFET) device, a metal semiconductor field effect transistor (MESFET) or other transconductor or transistor technology device. Such devices may use the same or alternative configurations other than the configuration illustrated in embodiments presented herein.

VII. Conclusion

While various embodiments have been described above, it should be understood that they have been presented by way of example only, and not limitation. It will be apparent to persons skilled in the relevant art that various changes in form and detail can be made therein without departing from the spirit and scope of the embodiments. Thus, the breadth and scope of the embodiments should not be limited by any of the above-described exemplary embodiments, but should be defined only in accordance with the following claims and their equivalents.

What is claimed is:

1. A system, comprising:
   a memory configured to store program instructions; and
   at least one processor configured to execute the program instructions to perform a method comprising:
   receiving a document that includes clinical information and that is structured in accordance with a first standard format, the first standard format being CCDA (Consolidated Clinical Document Architecture);
   generating an object model document to include at least one information-value pair of a plurality information-value pairs that each comprise an information identifier and an associated value string that are included in the document;
   assigning path definitions for each of the at least one information-value pair that define mappings between the at least one information-value pair in the object model document and objects of an ontology model having a second standard format, the second standard format being FHIR (Fast Healthcare Interoperability Resources), and the ontology model having a hierarchical structure based on attributes and dependency associations between objects therein;
   generating an instance model of the ontology model that is representative of the document and that is in the second standard format based on the path definitions by:
   linking the defined mappings to codes of the ontology model by traversing paths within the hierarchical structure of the ontology model specified by the path definitions;
   creating the objects for the instance model at endpoints of the paths that are traversed; and
   providing values to the objects for the instance model corresponding to each of the at least one information-value pair based on said linking; and
   responsive to receiving an object model query for at least one of the values, applying the object model query against the instance model that is generated, based on the attributes and the dependency associations of the objects, to generate a query result that comprises the at least one of the values.

2. The system of claim 1, the method further comprising: generating resources in accordance with the second standard format from the objects for the instance model.

3. The system of claim 1, wherein creating objects for the instance model comprises:
   creating a number of objects based on a request for information that corresponds to a same number of information-value pairs.

4. The system of claim 1, the method further comprising: generating a FHIR resource bundle, that includes the clinical information represented in the document, as FHIR resources within a FHIR document resource.

5. The system of claim 4, the method further comprising: storing the FHIR resource bundle in a database; and providing access to the database to accept queries for specific ones of the FHIR resources.

6. The system of claim 1, wherein the document is one of a plurality of documents in accordance with the first standard format that are stored in a repository, and
   wherein a first information identifier of a first information-value pair in a first section of the document is the same as a second information identifier of a second information-value pair in a second section of another document in the repository.

7. The system of claim 1, wherein the ontology model comprises a resource description framework (RDF) model.

8. A computer-implemented method, comprising:
   receiving a document that includes clinical information and that is structured in accordance with a first standard format, the first standard format being CCDA (Consolidated Clinical Document Architecture);
   generating an object model document to include at least one information-value pair of a plurality information-value pairs that each comprise an information identifier and an associated value string that are included in the document;

assigning path definitions for each of the at least one information-value pair that define mappings between the at least one information-value pair in the object model document and objects of an ontology model having a second standard format, the second standard format being FHIR (Fast Healthcare Interoperability Resources), and the ontology model having a hierarchical structure based on attributes and dependency associations between objects therein;

generating an instance model of the ontology model that is representative of the document and that is in the second standard format based on the path definitions by:
- linking the defined mappings to codes of the ontology model by traversing paths within the hierarchical structure of the ontology model specified by the path definitions;
- creating the objects for the instance model at endpoints of the paths that are traversed; and
- providing values to the objects for the instance model corresponding to each of the at least one information-value pair based on said linking; and responsive to receiving an object model query for at least one of the values, applying the object model query against the instance model that is generated, based on the attributes and the dependency associations of the objects, to generate a query result that comprises the at least one of the values.

9. The computer-implemented method of claim 8, the method further comprising:
generating resources in accordance with the second standard format from the objects for the instance model.

10. The computer-implemented method of claim 8, wherein creating objects for the instance model comprises:
creating a number of objects based on a request for information that corresponds to a same number of information-value pairs.

11. The computer-implemented method of claim 8, wherein the method further comprises:
generating a FHIR resource bundle, that includes the clinical information represented in the document, as FHIR resources within a FHIR document resource.

12. A computer-readable storage medium encoded with program instructions that, when executed by one or more processors, performs a computer-implemented method, comprising:
receiving a document that includes clinical information and that is structured in accordance with a first standard format, the first standard format being CCDA (Consolidated Clinical Document Architecture);
generating an object model document to include at least one information-value pair of a plurality information-value pairs that each comprise an information identifier and an associated value string that are included in the document;
assigning path definitions for each of the at least one information-value pair that define mappings between the at least one information-value pair in the object model document and objects of an ontology model having a second standard format, the second standard format being FHIR (Fast Healthcare Interoperability Resources), and the ontology model having a hierarchical structure based on attributes and dependency associations between objects therein;
generating an instance model of the ontology model that is representative of the document and that is in the second standard format based on the path definitions by:
- linking the defined mappings to codes of the ontology model by traversing paths within the hierarchical structure of the ontology model specified by the path definitions;
- creating the objects for the instance model at endpoints of the paths that are traversed; and
- providing values to the objects for the instance model corresponding to each of the at least one information-value pair based on said linking; and responsive to receiving an object model query for at least one of the values, applying the object model query against the instance model that is generated, based on the attributes and the dependency associations of the objects, to generate a query result that comprises the at least one of the values.

13. The computer-readable storage medium of claim 12, the method further comprising:
generating resources in accordance with the second standard format from the objects for the instance model.

14. The computer-readable storage medium of claim 12, wherein creating objects for the instance model comprises:
creating a number of objects based on a request for information that corresponds to a same number of information-value pairs.

15. The computer-readable storage medium of claim 12, the method further comprising:
generating a FHIR resource bundle, that includes the clinical information represented in the document, as FHIR resources within a FHIR document resource.

16. The computer-readable storage medium of claim 15, the method further comprising:
storing the FHIR resource bundle in a database; and
providing access to the database to accept queries for specific ones of the FHIR resources.

17. The computer-readable storage medium of claim 12, wherein the document is one of a plurality of documents in accordance with the first standard format that are stored in a repository, and
wherein a first information identifier of a first information-value pair in a first section of the document is the same as a second information identifier of a second information-value pair in a second section of another document in the repository.

18. The computer-readable storage medium of claim 12, wherein the ontology model comprises an RDF model.

* * * * *